(12) United States Patent
Shallenberg et al.

(10) Patent No.: US 11,039,930 B2
(45) Date of Patent: Jun. 22, 2021

(54) HIP IMPLANT SYSTEM

(71) Applicant: Encore Medical, L.P., Austin, TX (US)

(72) Inventors: Adam Shallenberg, Austin, TX (US); Stuart L. Axelson, Succasunna, NJ (US); R. Michael Meneghini, Indianapolis, IN (US); Scott Sporer, Winfield, IL (US); Michael Taunton, Rochester, MN (US); James Andrew Browne, Charlottesville, VA (US); Raymond Kim, Vail, CO (US); Paul K. Edwards, Little Rock, AR (US); Michael Mason, Brighton, MA (US); Joseph Jankiewicz, San Diego, CA (US); Mark McBride, San Diego, CA (US)

(73) Assignee: ENCORE MEDICAL, L.P., Austin, TX (US)

( * ) Notice: Subject to any disclaimer, the term of this patent is extended or adjusted under 35 U.S.C. 154(b) by 0 days.

(21) Appl. No.: 15/901,823

(22) Filed: Feb. 21, 2018

(65) Prior Publication Data

US 2018/0235763 A1   Aug. 23, 2018

Related U.S. Application Data

(60) Provisional application No. 62/462,829, filed on Feb. 23, 2017.

(51) Int. Cl.
*A61F 2/32* (2006.01)
*A61F 2/36* (2006.01)
(Continued)

(52) U.S. Cl.
CPC ............ *A61F 2/3607* (2013.01); *A61F 2/367* (2013.01); *A61F 2/3609* (2013.01);
(Continued)

(58) Field of Classification Search
CPC .... A61F 2002/30332; A61F 2220/0033; A61F 2002/365; A61F 2002/3611;
(Continued)

(56) References Cited

U.S. PATENT DOCUMENTS 5,906,644 A * 5/1999 Powell ................. A61F 2/3609
623/20.15
8,029,573 B2 10/2011 Podolsky
(Continued)

FOREIGN PATENT DOCUMENTS

FR   2 983 061 A1   5/2013
WO   WO 95/13757    5/1995

OTHER PUBLICATIONS

Invitation to Pay Additional Fees dated May 25, 2018 for PCT/US2018/019259, filed Feb. 22, 2018.
(Continued)

*Primary Examiner* — Ann Schillinger
(74) *Attorney, Agent, or Firm* — Knobbe, Martens, Olson & Bear LLP

(57) ABSTRACT

Hip implant systems described herein can include a distal stem, a proximal body, and a fastener. In some embodiments, the distal stem can include a cavity configured to receive the fastener when a portion of the distal stem is positioned within the proximal body. In some embodiments, the distal stem can include a threaded exterior surface configured to mate with a fastener when a portion of the distal stem is positioned within the proximal body. In some embodiments, a distal end of the distal stem can include an anterior relief configured to conform to interior surface of a femoral canal of a patient.

22 Claims, 26 Drawing Sheets

(51) Int. Cl.
*A61F 2/30* (2006.01)
*A61B 17/84* (2006.01)

(52) U.S. Cl.
CPC .......... *A61F 2/3676* (2013.01); *A61B 17/842* (2013.01); *A61F 2002/30332* (2013.01); *A61F 2002/30405* (2013.01); *A61F 2002/30507* (2013.01); *A61F 2002/30594* (2013.01); *A61F 2002/30604* (2013.01); *A61F 2002/30881* (2013.01); *A61F 2002/30884* (2013.01); *A61F 2002/3652* (2013.01); *A61F 2002/3686* (2013.01); *A61F 2310/00017* (2013.01); *A61F 2310/00023* (2013.01); *A61F 2310/00029* (2013.01)

(58) Field of Classification Search
CPC .. A61F 2002/3625; A61F 2/36; A61F 2/3609; A61F 2220/0025; A61F 2/3662; A61F 2/32; A61F 2/40; A61F 2/3676; A61F 2002/4681; A61F 2/4014; A61F 2002/30112; A61F 2002/4018; A61F 2002/4044; A61F 2/4607; A61F 2/3859; A61F 2/4059
See application file for complete search history.

(56) References Cited

U.S. PATENT DOCUMENTS

| | | | |
|---|---|---|---|
| 8,821,503 B2 | 9/2014 | Tornier et al. | |
| 8,974,540 B2 | 3/2015 | Podolsky | |
| 9,662,219 B2* | 5/2017 | Bonin, Jr. | A61B 17/0401 |
| 2005/0004679 A1* | 1/2005 | Sederholm | A61F 2/30734 |
| | | | 623/22.42 |
| 2011/0046745 A1 | 2/2011 | Daniels et al. | |
| 2011/0218640 A1* | 9/2011 | Smith | A61F 2/468 |
| | | | 623/22.42 |
| 2011/0257758 A1* | 10/2011 | Smith | A61F 2/3662 |
| | | | 623/22.42 |
| 2015/0305877 A1 | 10/2015 | Gargac et al. | |

OTHER PUBLICATIONS

International Search Report of PCT Application No. PCT/US2018/019259, dated Jul. 30, 2018.

* cited by examiner

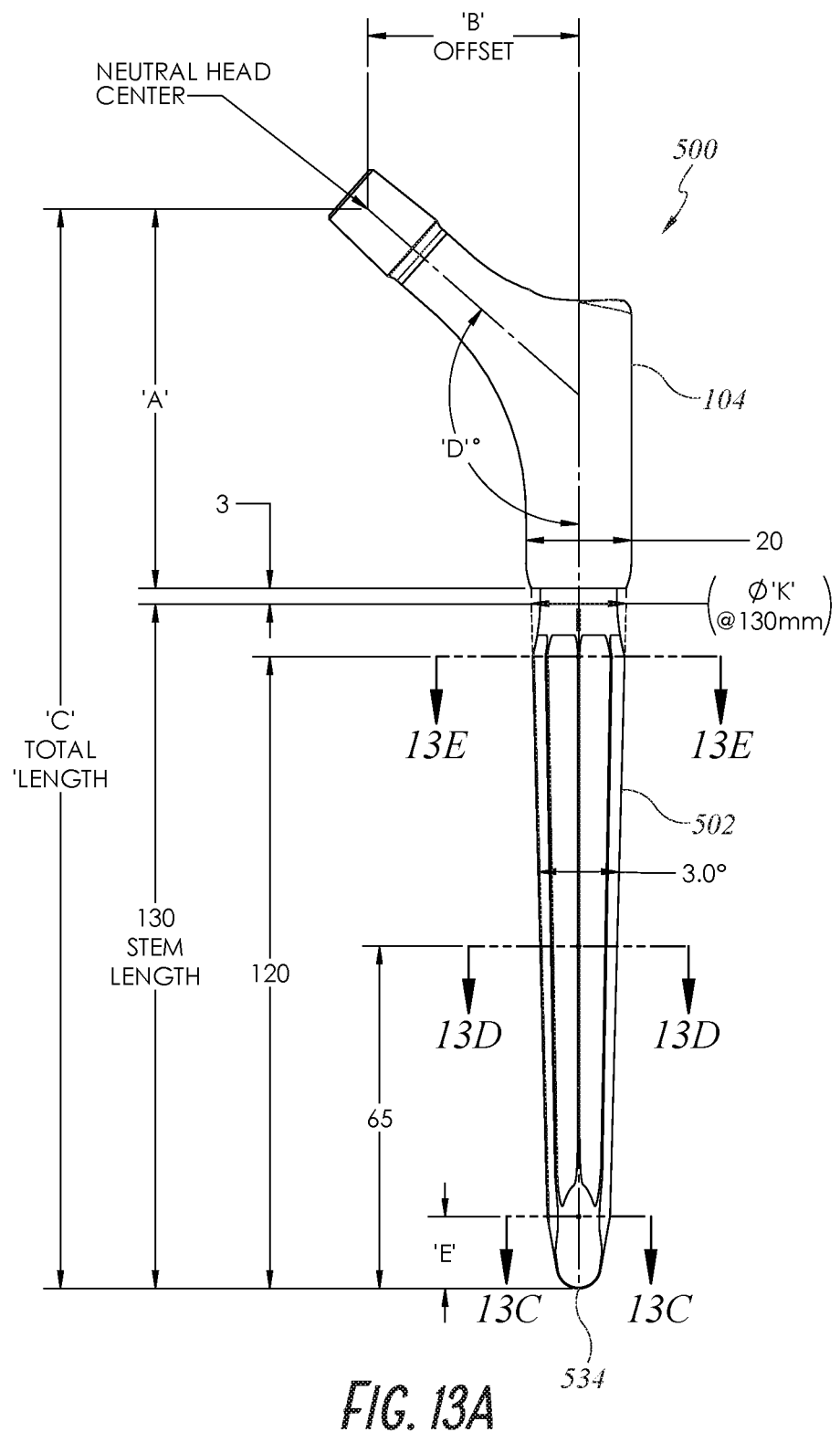
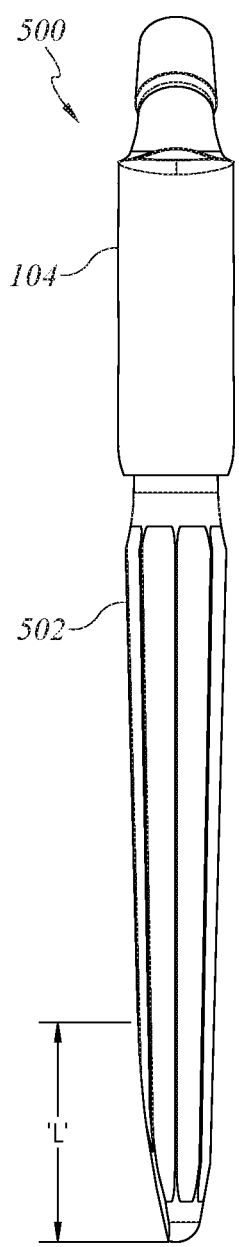
FIG. 13A
FIG. 13B

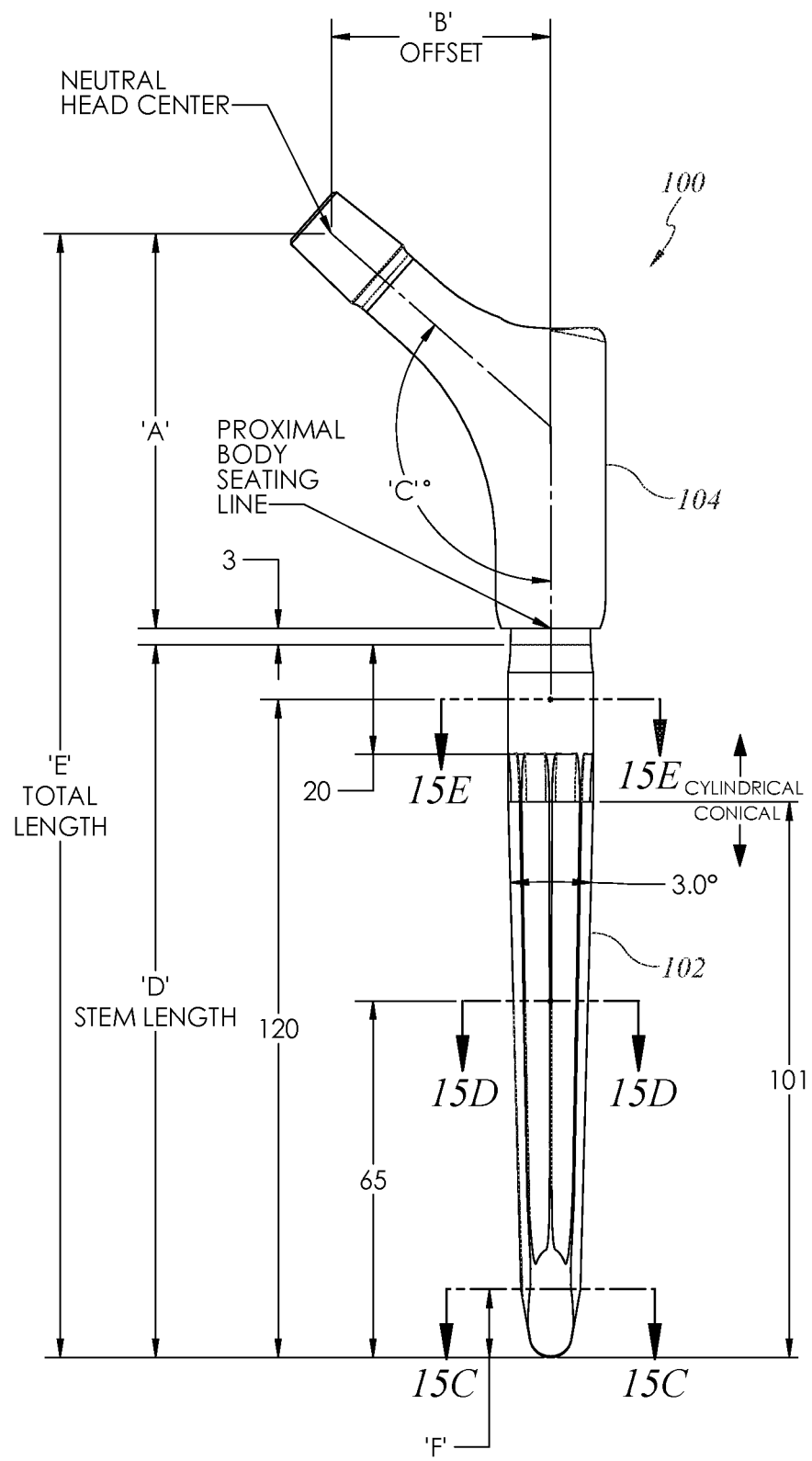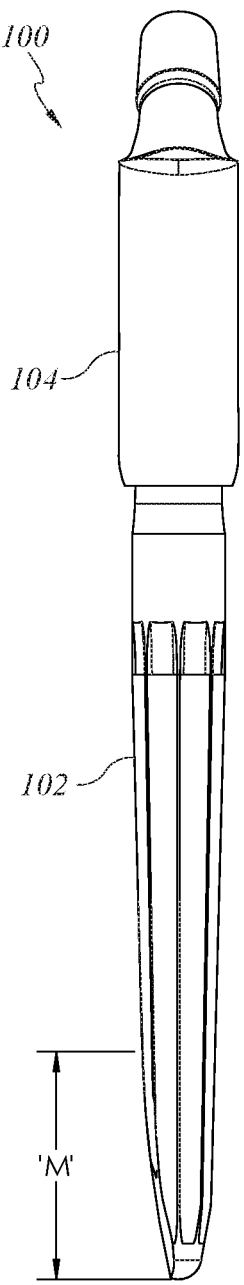
FIG. 15A
FIG. 15B

HIP IMPLANT SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims the benefit of U.S. Provisional Patent Application No. 62/462,829, filed Feb. 23, 2017, entitled "HIP IMPLANT SYSTEM," the content of which is hereby incorporated by reference in its entirety.

BACKGROUND

Field

This invention generally relates to prosthetic implants for both primary and revision hip applications. More specifically, this invention generally relates to systems of prosthetic implants, for example, systems that may include a stem, a proximal body, and a fastener.

Description of the Related Art

A damaged hip joint can cause pain and decreased mobility and may necessitate hip replacement surgery. Hip replacement surgery involves removal of at least part of a hip joint and replacement with a prosthetic implant. In a partial hip replacement surgery, or hemiarthroplasty, the femoral head of a damaged hip joint is removed and replaced with a prosthetic implant. In a total hip replacement surgery, both the femoral head and the acetabulum of the damaged hip joint are replaced. With revision total hip replacement surgery, it is common practice to remove the primary implants due to wear & tear, loosening infection or leg length discrepancies with primary surgery. Upon removal of the primary implants the remaining proximal femur is carefully machined (refined) to accept revision implant components. Modular, tapered revision stems (Wagner-style) have begun the popular implant choice as it accommodates diaphysis fixation while accommodating proximal stem-trunnion position via modular adjustments.

A prosthetic implant for hip replacement surgery can include a femoral stem component, a femoral head component, and, in instances of total hip replacement, an acetabular component. The femoral head component connects to the femoral stem component and can be secured to the femur by introduction of the femoral stem component into a femoral canal after the head and neck of the femur have been removed and the femoral canal has been reamed. The femoral head component is positioned to engage the acetabulum or, in instances of total hip replacement, the acetabular component that is attached to the acetabulum following removal of undesired portions. The size of the femoral canal, even when reamed, it limited by it structure, where enlarging it too much weakens the walls of the femur surrounding the femoral canal. Improvements on the structure of femoral stem component are desired to help alleviate the amount of reaming of the femoral canal.

SUMMARY

Several innovations are disclosed herein, each having multiple aspects that can be included in various embodiments of the innovations. For example, one innovation is a hip implant system having an elongated distal stem that includes a tapered trunnion having a proximal end, a distal end, and a longitudinal axis extending therebetween. The tapered trunnion can further include an inner cavity defined by an interior surface of the tapered trunnion and extending from the proximal end of the tapered trunnion through at least a portion of the tapered trunnion. The interior surface of the tapered trunnion may include a threaded portion configured to mate with a threaded end of a fastener. The distal stem can further include a stem body having a proximal end and a distal end, the stem body extending distally from the tapered trunnion. The hip implant system can further include a proximal body. The proximal body can include a body distal end, a first opening on one side of the proximal body at the body distal end, a second opening positioned opposite the first opening on the other side of the proximal body, and an inner cavity extending in the proximal body between the first opening and the second opening, the inner cavity defined by an interior surface of the proximal body. The inner cavity can include a first inner cavity section positioned proximal to the first opening, wherein the proximal body is configured to receive the proximal end of the tapered trunnion of the distal stem through the first opening and within the first inner cavity section, and a second inner cavity section positioned proximal to the second opening between the first inner cavity and the second opening, wherein the interior surface in the second inner cavity section includes a circumference smaller than a circumference of the interior surface in the first inner cavity section, wherein the circumference of the interior surface in the second inner cavity section is smaller than an outer circumference of the proximal end of the tapered trunnion of the distal stem. The proximal body may further include a neck portion extending laterally and proximally from a side of the proximal body, the neck portion being configured to engage a femoral head. The hip implant system can further include a fastener. The fastener, elongated distal stem and a proximal body are collectively configured to allow the fastener to be placed through an aperture in the proximal body and into the tapered trunnion portion of the elongated distal stem, and when tightened securely connecting the proximal body to the elongated distal stem. The fastener can include a head configured to engage a tool for tightening and loosening the fastener, a threaded end, and a shaft extending between the head and the threaded end, wherein at least a portion of the threaded end is configured to extend through the second inner cavity section and mate with the threaded portion of the interior surface of the tapered trunnion.

In some embodiments, the distal stem can include a plurality of ridges disposed on the exterior surface of the stem body. In some embodiments, the distal end of the stem body can include a partially rounded distal tip including a front section and a rear section, the front and rear sections separated by a coronal plane extending through the stem body from a proximal end of the stem body to the distal end of the stem body, wherein the rear section of the distal tip is characterized by a partially spherical shape, wherein the front section of the distal tip includes an anterior relief having an elongated face having a rounded distal edge, wherein at least a portion of the anterior relief is configured to taper towards the distal end at a greater angle than a segment of the stem body immediately proximal to the anterior relief. In some embodiments, the exterior surface of the proximal body includes at least one groove configured to receive poly cabling (such a groove may be referred to herein as a "cable groove" for ease of reference). The cable groove is useful, for example, as a structure to hold poly cabling that is wrapped around the proximal body and also around a portion of a patient's body so that the poly cabling does not move along the surface of the proximal body. For example, poly cabling may be wrapped around the proximal body and the patient's femur, and the cable groove receives a portion of the poly cabling in the groove to secure the poly cabling from moving along a smooth, hard and curved surface of the proximal body. Some embodiments may include a single groove, where other embodiments may include 2, 3, 4, 5 or more cable grooves. The cable groove is structured as an indentation (or channel) on a portion of the surface of the proximal body, having a selected depth and width to allow one or more cables to be placed in the cable groove. In some embodiments, the at least one groove is at least 0.01 mm deep and at least 0.01 mm wide, although in many applications the at least one groove is much larger, for example, in the range of about 0.1 mm to 0.8 mm (wide and/or deep). In some embodiments, the grooves are normal to medial calcar surface or angles. In some embodiments, each groove is sized to receive two kinamed poly cables of 0.0625 inches in diameter (or about 1.5 mm in diameter). In some embodiments, the at least one groove is 0.20 inches deep and wide (or about 0.5 mm). In some embodiments, the second inner cavity is configured to receive the threaded body of the fastener, wherein the interior surface of the proximal body at the second inner cavity includes a threaded section configured to mate with a threaded bolt of a taper breaker. In some embodiments, the longitudinal axis of the stem body is positioned at a non-zero angle to the longitudinal axis of the tapered trunnion.

Another innovation is a hip implant system including an elongated distal stem having a tapered trunnion having a proximal end, a distal end, and a longitudinal axis extending therebetween. An exterior surface of the tapered trunnion includes a threaded portion configured to mate with a fastener. The elongated distal stem can further include a stem body section including a proximal end, a distal end, and a longitudinal axis extending therebetween, the stem body extending distally from the tapered trunnion. The hip implant system can further include a proximal body. The proximal body can include a body distal end, a first opening on one side of the proximal body at the body distal end, a second opening positioned opposite the first opening on the other side of the proximal body, and an inner cavity extending in the proximal body between the first opening and the second opening, the inner cavity defined by an interior surface of the proximal body. The proximal body is configured to receive the proximal end of the tapered trunnion through the first opening and within the inner cavity and at least a portion of the fastener through the second opening and within the inner cavity. The proximal body can further include a neck portion extending laterally and proximally from a side of the proximal body, the neck portion being configured to engage a femoral head. The hip implant system can further include the fastener. The fastener can include a proximal end and a distal end, the distal end of the fastener being configured to extend through the inner cavity of the proximal body to mate with the threaded portion of the tapered trunnion of the elongated distal stem within the inner cavity of the proximal body and an inner cavity defined by an interior surface of the fastener and extending from the distal end of the fastener at least partially toward the proximal end of the fastener through at least a portion of the fastener, wherein the interior surface of the fastener includes a threaded portion configured to mate with threaded portion of the tapered trunnion of the elongated distal stem.

In some embodiments, the distal stem may include a plurality of ridges disposed on the exterior surface of the stem body. In some embodiments, the distal end of the stem body includes a partially rounded distal tip having a front section and a rear section, the front and rear sections being separated by a coronal plane extending through the stem body from a proximal end of the stem body to the distal end of the stem body. The rear section of the distal tip may be characterized by a partially spherical shape, wherein the front section of the distal tip includes an anterior relief, the anterior relief having an elongated face having a rounded distal edge. At least a portion of the anterior relief may be configured to taper towards the distal end at a greater angle than a segment of the stem body immediately proximal to the anterior relief. In some embodiments, an exterior surface of the proximal body includes at least one groove configured to receive poly cabling. In some embodiments, the longitudinal axis of the stem body is positioned at a non-zero angle to the longitudinal axis of the tapered trunnion. In some embodiments, the fastener and the proximal body each further include a corresponding inclined contact face that mate with each other when the fastener is tightened on the threaded portion of the tapered trunnion of the elongated distal stem, the inclined contact face of the fastener disposed on an exterior surface of the fastener and the inclined contact face of the proximal body being disposed within the second opening along a surface of the inner cavity.

BRIEF DESCRIPTION OF THE DRAWINGS

FIG. 13A depicts a front view a hip implant system in accordance with an illustrative embodiment.

FIG. 13B depicts a side view of a hip implant system in accordance with an illustrative embodiment.

FIG. 15A depicts a front view a hip implant system in accordance with an illustrative embodiment.

FIG. 15B depicts a side view of a hip implant system in accordance with an illustrative embodiment.

DETAILED DESCRIPTION

The following detailed description is directed to certain specific embodiments of the invention. However, the invention can be embodied in a multitude of different ways. It should be apparent that the aspects herein may be embodied in a wide variety of forms and that any specific structure, function, or both being disclosed herein is merely representative of one or more embodiments of the invention. An aspect disclosed herein may be implemented independently of any other aspects and that two or more of these aspects may be combined in various ways. For example, an apparatus (e.g., the illustrated embodiments a distal stem or a proximal body) may be implemented, or a method may be practiced, using any number of the aspects set forth herein. In addition, such an apparatus may be implemented or such a method may be practiced using other structure, functionality, or structure and functionality in addition to, or other than one or more of the aspects set forth herein.

Figure 1:
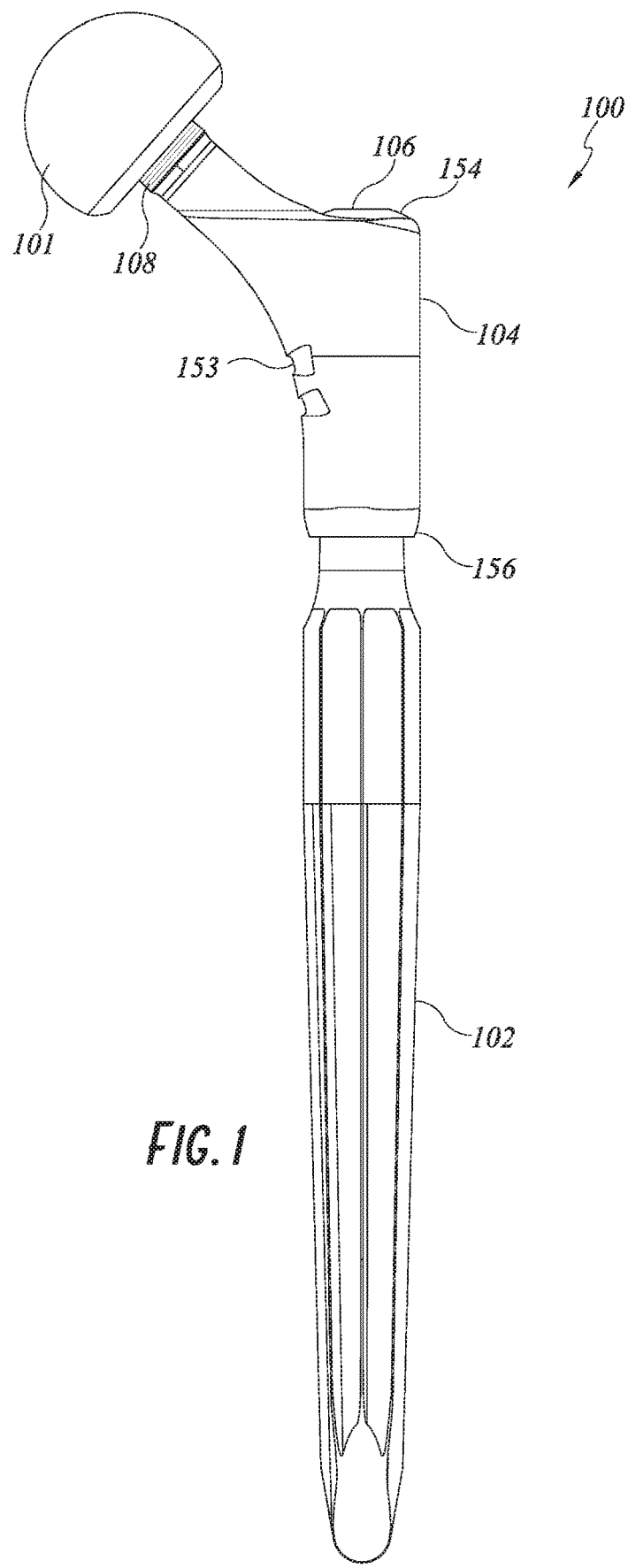
FIG. 1 depicts a front view of a hip implant system in accordance with an illustrative embodiment.

FIG. 1 depicts an example of a hip implant system 100, in accordance with some embodiments. The illustrated hip implant system 100 includes an elongated distal stem 102 (sometimes referred to herein as "distal stem" for ease of reference), a proximal body 104, a fastener 106, and a femoral head 101. Reference to a "hip implant system" as used herein generally refers to at least two components, for example, a hip implant system as referred to herein may include the proximal body 104 and the elongated distal stem 102. In another example, a hip implant system as referred to herein may include the proximal body 104, the elongated distal stem 102, and the fastener 106.

The hip implant system 100 can be configured for placement in the human body as part of a partial or total hip replacement surgery to replace at least part of a damaged hip joint. The distal stem 102 can securably engage the proximal body 104. To facilitate engagement, the proximal end of the distal stem 102 can be received within a distal end 156 of the proximal body 104, as described further herein. The fastener 106 can secure the distal stem 102 to the proximal body 104. In some embodiments, the fastener 106 can extend through a proximal end 154 of the proximal body 104 to engage a proximal end of the distal stem 102, as described further herein, for example, in reference to FIGS. 6-8C. During hip replacement surgery, the distal stem 102 is configured to be introduced into a femoral canal of a femur. A neck portion 108 of the proximal body 104 can be securably engaged to the femoral head 101 which can be received in an acetabulum of the hip or in a prosthetic acetabular component. The acetabular component can be an acetabular cup. The acetabular cup can be a single-piece acetabular cup or a modular acetabular cup. In some embodiments, a modular acetabular cup can include a shell and a liner (not shown). In some embodiments, the femoral head 101 can be a component of an acetabular system, such as the X-Alt™ acetabular system, the Biolox® delta acetabular system, or the FMP® acetabular system, each manufactured by DJO Global, Inc. When implanted, the hip implant system 100 is configured to perform one or more functions of the hip joint, and can provide increased mobility and reduced pain in a patient suffering from hip joint damage, such as that resulting from osteoarthritis.

Figure 2:
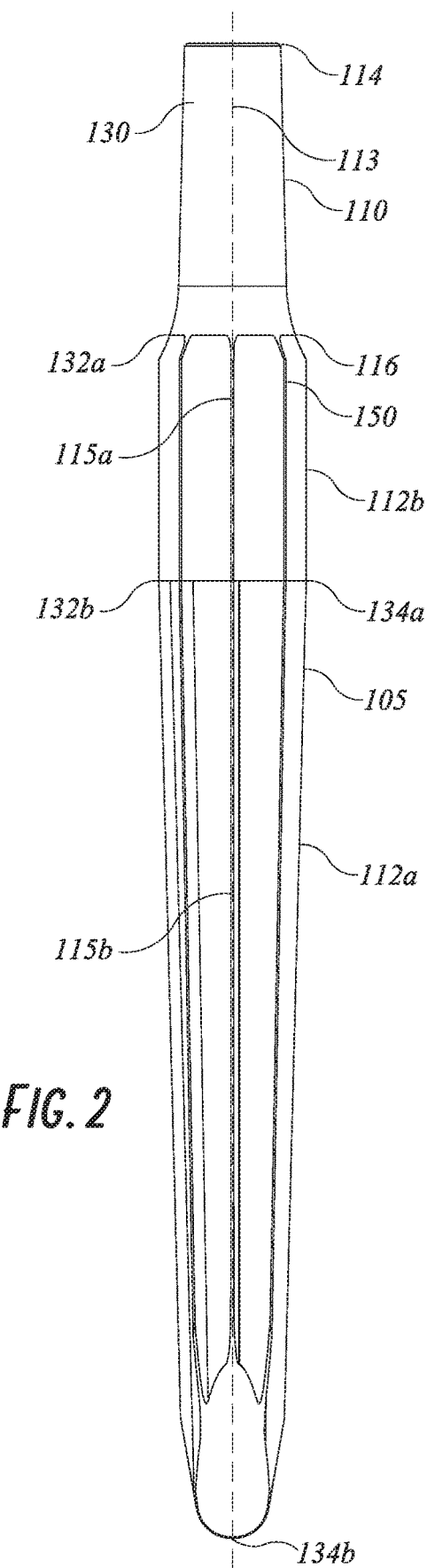
FIG. 2 depicts a front view of a distal stem in accordance with an illustrative embodiment.
Figure 3A:
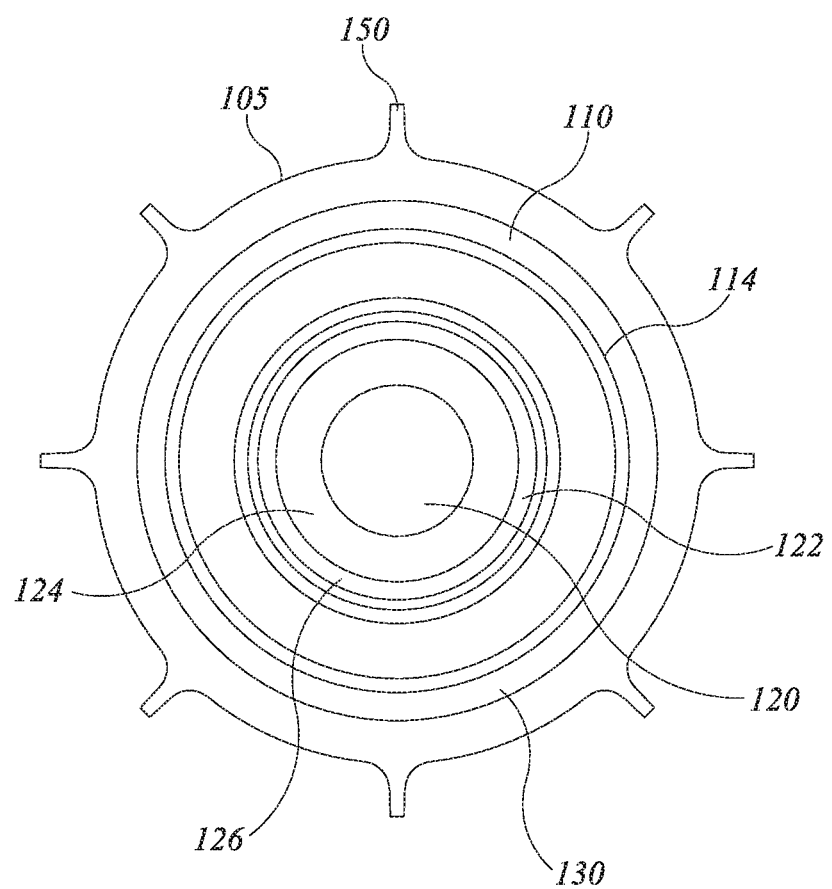
FIG. 3A depicts a top view of a distal stem in accordance with an illustrative embodiment.
Figure 3B:
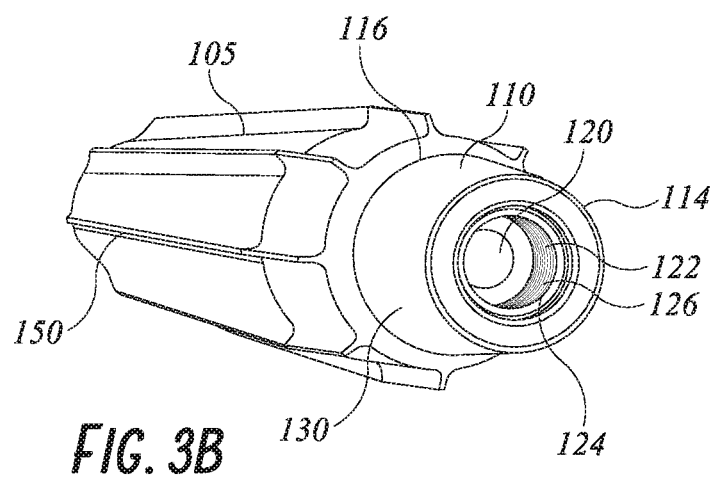
FIG. 3B depicts a top perspective view of a distal stem in accordance with an illustrative embodiment.
Figure 4:
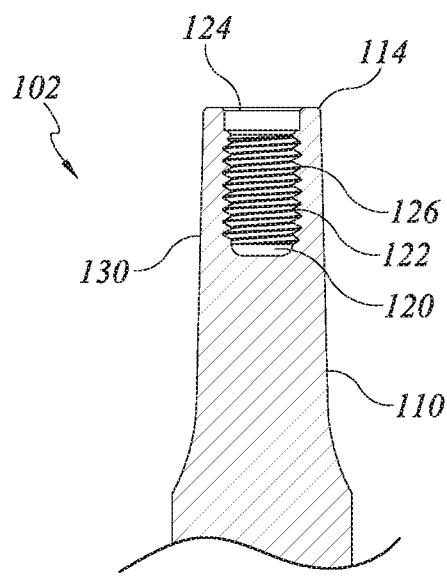
FIG. 4 depicts a cross-sectional view of a section of a distal stem in accordance with an illustrative embodiment.

FIGS. 2-5C depict the distal stem 102 in accordance with certain embodiments. FIGS. 2, 3A, and 3B depict a front view, a top view, and a top perspective view, respectively, of the distal stem 102. The distal stem 102 includes a tapered trunnion 110 and stem body 105. FIG. 4 depicts a cross-sectional view of the tapered trunnion 110. The tapered trunnion 110 includes a proximal end 114, a distal end 116, and a longitudinal axis 113 (illustrated by a dashed line) extending therebetween. The tapered trunnion 110 also includes an inner cavity 120. The inner cavity 120 is defined by an interior surface 122 of the tapered trunnion 110. The inner cavity 120 extends from an opening 124 at the proximal end 114 of the tapered trunnion 110 at least partially toward the distal end 116 of the tapered trunnion 110 through at least a portion of the tapered trunnion 110. In some embodiments, the interior surface 122 of the tapered trunnion 110 includes a threaded portion 126 having one or more threads or grooves for receiving the fastener 106. The tapered trunnion 110 further includes an exterior surface section 130 near the proximal end of the tapered trunnion 110 configured to be received by the proximal body 104. In some embodiments, the exterior surface section 130 is sized and/or shaped to securably engage the proximal body 104. For example, the exterior surface section 130 can be substantially cylindrical.

The stem body 105 includes first body section 112a and a second body section 112b. The second body section 112b includes a proximal end 132a, a distal end 132b, and a longitudinal axis 115a (illustrated by a dashed line) extending therebetween. The second body section 112b extends distally from the distal end 116 of the tapered trunnion 110. In the embodiment illustrated in FIG. 2, the longitudinal axis of the second body section 112b is aligned with or generally aligned with the longitudinal axis of the tapered trunnion 110.

The first body section 112a includes a proximal end 134a, a distal end 134b, and a longitudinal axis 115b (illustrated by a dashed line) extending therebetween. The first body section 112a extends distally from the distal end 132b of the second body section 112b.

The stem body 105 can be shaped and/or sized to allow the stem body 105 to be received within a femoral canal of various sizes for different patients. In some embodiments, the second body section 112b can have a generally uniform cross-section along the axis 115a. In some embodiments, the second body section 112b can be generally cylindrical.

The stem body 105 can have a length of 120 mm, 130 mm, 170 mm, 210 mm, or any other suitable size for implantation into the femoral canal. Some examples of these sized stem bodies are described in reference to FIGS. 13-16. In some embodiments, the first body section 112a can have a length of 120 mm or 130 mm. In some other examples, the first body section 112a can have a length any other suitable size.

As illustrated in the example of FIG. 2, at least a portion of the first body section 112a may be tapered such that a first circumference or cross-sectional area of the second body section 112a perpendicular to the longitudinal axis 115b of the first body section 112a is smaller than a second circumference or cross-sectional area of the first body section 112a perpendicular to the longitudinal axis positioned proximal to the first circumference or cross sectional area of the first body section 112a. In some embodiments, the first body section 112a tapers at a 3° angle from the proximal end 134a to the distal end 134b of the first body section 112a.

The stem body 105 may be fluted having structural features that extend outward (or inward) from a surface of the stem body 105. For example, the stem body may include one or more ridges or fins 150 (both being referred to as "fins" for ease of reference) extending longitudinally along the stem body 105. Although it is possible for a stem body 105 to have only one fin 150, most embodiments include a plurality of fins 150 configured to engage an interior surface of the femoral canal. By engaging the interior surface of the femoral canal, the fins 150 can stabilize the distal stem 102 within the femoral canal. In addition, the fins 150 provide a separation between a surface of the femoral canal and the stem body 105 such that a space is formed, which may allow growth of bone or tissue around the distal stem 102 to help secure the distal stem 102 to the femoral canal.

In some embodiments, only a portion of the body 105 may include one or more fins 150. For example, in some embodiments only the first body section 112a includes one or more fins 150. A second body section 112b having fins 150 and having a total diameter measurement that includes the length of the fins 150 may be structurally weaker than a second body section 112b without fins and having a diameter equivalent to the total diameter measurement diameter measurement of the second body section 112b having fins 150. In some embodiments, the second body section 112b may be provided without fins 150 in order to provide a smaller diameter of the second body section 112b while maintaining structural stability. Examples of embodiments having a second body section 112b without fins 150 are described with respect to FIGS. 15A-E below. In some embodiments, only the second body section 112b includes one or more fins 150. In some embodiments, one or more fins extend from the proximal end 132a of the second body section 112b to the distal end 134b of the first body section 112a. In some embodiments, one or more fins extend from a segment of the distal stem 102 that is 25 mm distal from the proximal end 114 to the distal end of the first body section 112a. In some embodiments, the distal stem 102 may not have fins positioned between the proximal end 114 and a segment of the distal stem 102 that is 25 mm distal from the proximal end 114. In some embodiments, the distal stem 102 is sized such that there is an interference of 0.20 mm radially between the fins 112 and the interior surface of the canal. By design, the outer most diameter of the fins 150 is larger than the reamed canal, for example by 0.40 mm (0.20 mm radially). The fins 150 can have a fin height beyond the core diameter (the diameter of the stem body at sections that do not include fins 150) of, for example, 0.5 mm, 0.68 mm, 0.95 mm, 1.0 mm, 1.5 mm, or another suitable height. The built-in interference (e.g., of 0.20 mm radially) affects the height of the distal stem 102 is final depth when fully seated. For example, the 0.20 mm nominal interference and having tight tolerance controls between the stem and reamer may yield a full seating range of −2.0 mm to 4.0 mm (that is, a 6.0 mm range) where the distal stem 102 may sit below or above the top of the reamed canal, or slightly projecting above of reamed canal. The −2.0 mm to 4.0 mm (e.g., a 6.0 mm range) relates to a tolerance of the distal stem 102 implant and the reamer used (for example, providing a worst case of least material and maximum material conditions).

The core diameter of stem body 105 at or near the proximal end of 134a of the first body section 112a (in some embodiments, for example, at a point 120 mm or 130 mm proximal to the distal end 134b of the first body section 112a) can be 14.5 mm, 15.5 mm, 16.0 mm. 16.5 mm, 17.0 mm, 17.5 mm, 18.0 mm, 18.5 mm, 19.0 mm, 20.0 mm, 20.5 mm, 21.0 mm, 22.0 mm, 23.0 mm, 24.0 mm, 25.0 mm, 27.0 mm or any other suitable diameter. The core diameter of stem body 105 at a point 65 mm or about 65 mm proximal to the distal end 134b can be 11.2 mm, 12.2 mm, 12.6 mm, 13.6 mm, 14.6 mm, 15.6 mm, 17.6 mm, 19.6 mm, 21.6 mm, 23.6 mm or any other suitable diameter. The core diameter at a point 11.1 mm, 12.4 mm, 13.7 mm, 15.0 mm, 16.3 mm, 17.6 mm, 18.9 mm, 21.4 mm, 24.0 mm, 26.6 mm, or 29.2 mm proximal to the distal end 134b of the first body section 112a can be 7.9 mm, 9.0 mm, 9.0 mm, 11.0 mm, 12.1 mm, 13.2 mm, 15.3 mm, 17.5 mm, 19.6 mm, 21.7 mm, or any other suitable diameter.

Figure 5A:
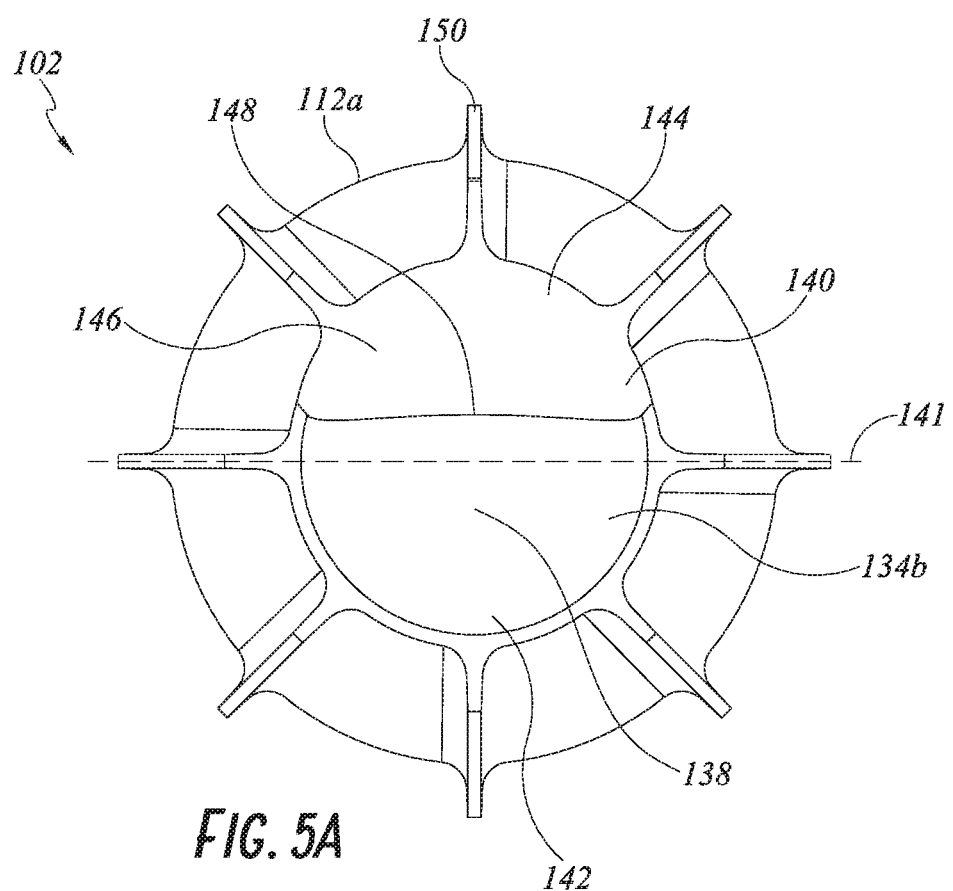
FIG. 5A depicts a bottom view of a distal stem in accordance with an illustrative embodiment.
Figure 5B:
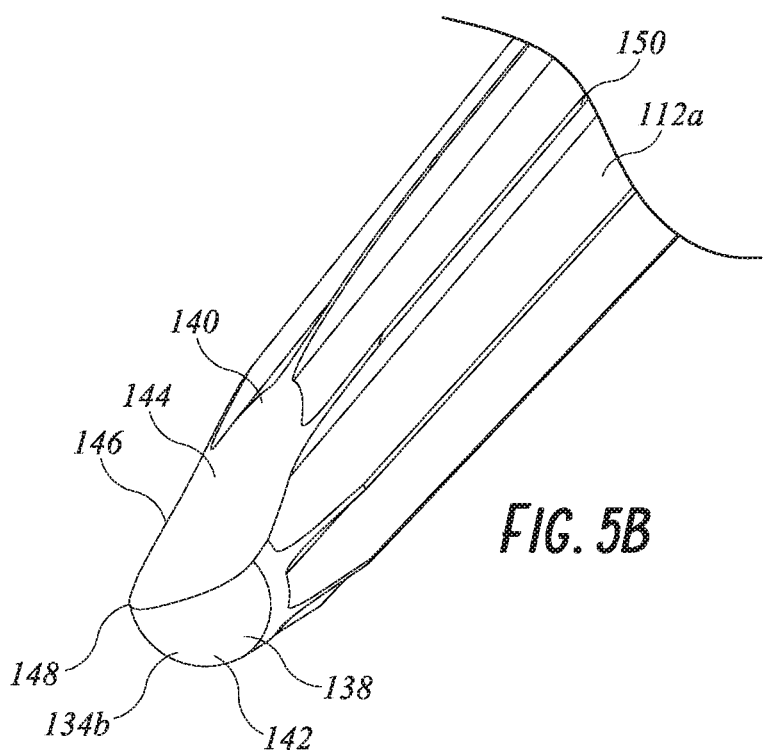
FIG. 5B depicts a front perspective view of a section of a distal stem in accordance with an illustrative embodiment.
Figure 5C:
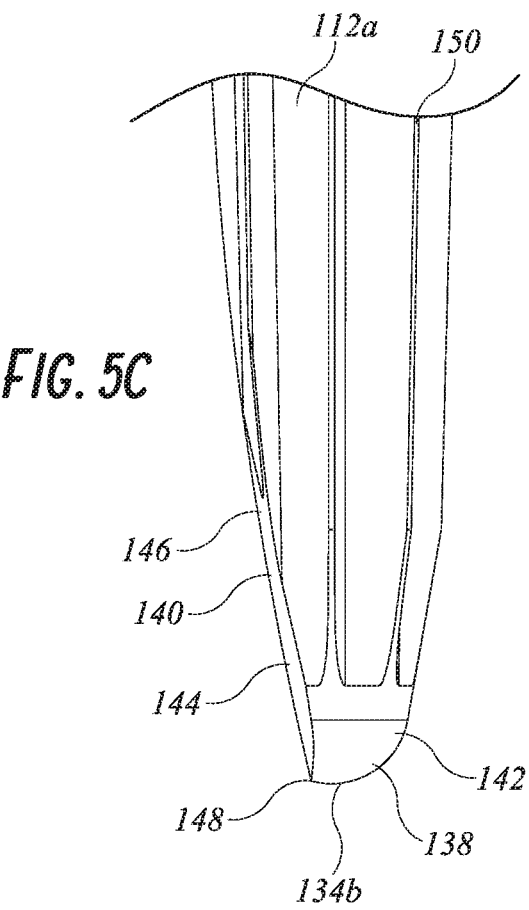
FIG. 5C depicts a side view of a section of a distal stem in accordance with an illustrative embodiment.

FIGS. 5A-C depict a front view, a perspective view, and a side view, respectively of a section of the first body section 112a near the distal end 134b of the first body section 112a in accordance with some embodiments. The distal end 134b of the first body section 112a can include a distal tip 138. The distal tip 138 can be shaped and/or sized to facilitate introduction into or fit within the femoral canal. In some embodiments, the distal tip 138 is shaped and/or sized to reduce impact and/or friction with an interior wall of the femoral canal during and/or after introduction of the distal stem 102. In some embodiments, the distal tip 138 can be partially rounded. For example, the distal tip 138 can be partially spherical in shape. As shown in FIG. 5C, the distal tip 138 includes a front section 140 and a rear section 142.

The front section 140 and rear section 142 are separated by a coronal plane 141 (illustrated by a dashed line) extending through the first body section 112*a* from the proximal end 134*a* of the first body section 112*a* (not shown in FIGS. 4 and 5) to the distal end 134*b* of the first body section 112*a*. The rear section 142 of the distal tip 138 can be characterized by a partially rounded shape. For example, the rear section 142 of the distal tip 138 can be partially spherical. In some embodiments, at least a portion of the rear section 142 is shaped as a quarter sphere. In some embodiments, a distal segment of the first body section 112*a* of the distal stem 102 is configured to taper towards the distal end 134*b* at a greater angle than a segment of the first body section 112*a* immediately proximal to the distal section.

The front section 140 of the distal tip 138 includes an anterior relief 144. The anterior relief 144 can be shaped and/or sized to facilitate introduction into or fit within the femoral canal. In some embodiments, the distal tip 138 is shaped and/or sized to reduce impact and/or friction within an interior wall of the femoral canal during and/or after introduction of the distal stem 102 into the femoral canal. The anterior relief 144 includes an elongated face 146. The elongated face 146 of the anterior relief 144 includes a rounded distal edge 148 at its distal most end. The elongated face 146 of the anterior relief 144 can extend to the distal end 134*b* of the first body section 112*a* or immediately proximal to the distal end 134*b* of the first body section 112*a*. In some embodiments, at least a portion of the anterior relief 144 is configured to taper towards the distal end 134*b* of the first body section 112*a* at a greater angle than a segment of the first body section 112*a* immediately proximal to the anterior relief 144.

The anterior relief 144 can be any shape suitable for introduction into and residence within the femoral canal. For example, the anterior relief 144 can be shaped to conform to the interior surface of the femur defining the femoral canal. In some embodiments, the elongated face 146 of the anterior relief 144 can be substantially flat. In some embodiments, the elongated face 146 can be circular, oval-shaped, diamond-shaped, square, triangular, or any other suitable shape. In some embodiments, the anterior relief 144 is at least partially convex along a cross-section perpendicular to the longitudinal axis of the first body section 112*a*. In some embodiments, the anterior relief 144 is at least partially concave along a cross-section perpendicular to the longitudinal axis of the first body section 112*a*. In some embodiments, the anterior relief 144 is at least partially concave along a cross-section parallel to the longitudinal axis of the first body section 112*a*. In some embodiments, the anterior relief 144 is at least partially concave along a cross-section parallel to the longitudinal axis of the first body section 112*a*. In some embodiments, the elongated face 146 of the anterior relief 144 can have a length of 38.1 mm, 50.8 mm, or any other suitable length.

FIGS. 6-8C depict a front perspective view, a bottom perspective view, and a top perspective view, respectively, of the proximal body 104 in accordance with some embodiments. The proximal body 104 includes a connection portion 152 and the neck portion 108. The connection portion 152 includes a proximal end 154, a distal end 156, and a longitudinal axis 111 (illustrated by a dotted line) extending therebetween. The distal end 156 of the connection portion 152 can be configured to engage the proximal end 114 of the tapered trunnion 110 of the distal stem 102. In some embodiments, the distal end 156 of the connection portion 152 includes a first opening 158 configured to receive the proximal end 114 of the tapered trunnion 110. The connection portion 152 also includes a second opening 160 at the proximal end 154 of the connection portion 152. The second opening 160 can be configured to receive the fastener 106.

The connection portion 152 of the proximal body 104 further includes an inner cavity 162 extending between the first opening 158 and the second opening 160. The inner cavity 162 is defined by an interior surface 164 of the connection portion 152. The interior surface 164 can include one or more interior surface sections defining one or more inner cavity sections. The one or more interior surface sections can include one or more different circumferences, diameters, cross-sections, and/or surface features, such as for example, threading, grooves, or textured sections.

With continued reference to FIGS. 6-8C, the interior surface 164 of the connection portion 152 includes a first interior surface section 166 defining a first inner cavity section 168 positioned immediately proximal to the first opening 158 of the connection portion 152 of the proximal body 104. The first inner cavity section 168 can be shaped and/or sized to receive the proximal end 114 of the tapered trunnion 110 of the distal stem 102. In some embodiments, the first inner cavity section 168 can be shaped/and or sized to facilitate mating of the first interior surface section 166 with the exterior surface section 130 of the tapered trunnion 110 of the distal stem 102. In some embodiments, the first interior surface section 166 is configured to securably engage the exterior surface section 130 of the tapered trunnion 110 of the distal stem 102. For example, the first interior surface section 166 can be configured to engage the exterior surface section 130 via an interference fit. In other embodiments, the first interior surface section 166 and exterior surface section 130 can each include complimentary threaded portions.

The inner cavity 162 can also include a second interior surface section 170 immediately proximal the first interior surface section 166, the second interior surface section 170 defining a second inner cavity section 172. In some embodiments, the second inner cavity section 172 has a circumference or cross-sectional area smaller than the circumference or cross-sectional area of the first inner cavity section 168. Accordingly, a circumference of the second interior surface section 170 can be less than a circumference of the first interior surface section 166. In some embodiments, a distal end of the second interior surface section 170 defines a lip 174. The circumference of the second interior surface section 170 can be less than an outer circumference of the proximal end 114 of the tapered trunnion 110 of the distal stem 102. In some embodiments, the proximal end 114 of the tapered trunnion 110 can be configured to abut the lip 174 defined by the distal end of the second interior surface section 170.

The second inner cavity section 172 can be configured to receive the fastener 106. In some embodiments, the second inner cavity section 172 is sized and/or shaped to allow passage of at least a portion of the fastener 106 through the second inner cavity section 172 to at least a portion of the first inner cavity section 168.

In some embodiments, the second inner cavity section 172 can include a threaded section 176. The threaded section 176 can include on or more threads, grooves or other surface features configured to engage with one or more complimentary threads, grooves, or other surface features of a tool, fastener, or other device inserted into the second opening 160 of the connection portion 152. For example, the threaded section 176 can be configured to mate with a threaded section of a taper breaker. In some embodiments, the threaded section 176 can be configured to mate with at least a portion of the threaded section of the fastener 106.

The inner cavity 162 further includes a third interior surface section 178 extending distally from the second opening 160 and defining a third inner cavity section 180. In some embodiments, the third interior section 178 can be positioned immediately proximal the second interior surface section 170. In some embodiments, the third inner cavity section 180 can be sized and/or shaped to receive a fastener, a tool, and/or one or more other devices. For example, the third inner cavity section 180 can be configured to allow for passage of portion of the fastener 106.

In some embodiments, the third inner cavity section 180 has a circumference or cross-sectional area greater than the circumference or cross-sectional area of the second inner cavity section 172. Accordingly, a circumference of the third interior surface section 178 can be greater than the circumference of the first interior surface section 166. In some embodiments, a proximal end of the second interior surface section 170 defines a spherical rim 182. The circumference of the second interior surface section 170 can be less than an outer circumference of at least a portion of the fastener 106. In some embodiments, the spherical rim 182 defined by the proximal end of the second interior surface section 170 can be configured to abut at least a portion of the fastener 106 when the fastener 106 is inserted into the proximal body 104. In some embodiments the spherical rim 182 defined by the proximal end of the second interior surface section 170 can include one or more recesses or other surface features for receiving one or more tools or other devices, such as for example, a taper breaker.

As explained in further detail herein, the second opening 160, third inner cavity section 180, and second inner cavity section 172 can be configured to allow for passage of a portion of the fastener 106 so that the fastener 106 can securably mate with the distal stem 102 and to prevent a passage of a portion of the fastener 106 into the second inner cavity section 172 such that the fastener 106 secures the proximal body 104 to distal stem 102.

The neck portion 108 of the proximal body 104 extends laterally and proximally from a side of the proximal body 104 and comprises a longitudinal axis 107 (illustrated by a dotted line). The neck portion 108 can be configured to engage a femoral head. In some embodiments, the neck portion 108 can include a grooved section 151 having one or more grooves, threads, or other surface features configured to mate with a femoral head, such as femoral head 101. In some embodiments, the grooved section 151 is configured to mate with a femoral head, such as femoral head 101 via a taper fit.

The proximal body 104 may include one or more structures that are configured to be a connection place for securing a cable to the proximal body 104. For example, the proximal body 104 illustrated in FIG. 6 further includes a pair of cable grooves 153 positioned on an edge 103 of the proximal body. For example, in the embodiment illustrated in FIG. 6 the cable grooves 153 extend into a portion of the surface 157 of the connection section 152. In various embodiments there may be one cable groove 153, or a plurality of cable grooves 153. In some embodiments, each cable groove 153 may be characterized as running along the generally cylindrical surface 157 of the connection section 152 in a plane that may be substantially normal to the longitudinal axis of the connection section 152. Each cable groove 153 can be configured to wrap partially around the exterior of the connection section 152. In some embodiments, each cable groove 153 can wrap around 5%, 10%, 15%, 20%, 25%, 30%, 35%, 40%, 50%, 55%, 60%, 65%, 70%, 75%, 80%, 85%, 90%, 95%, 100%, or any other suitable amount of the circumference of the connection section 152. In some embodiments, the proximal body 104 can further include one or more cable grooves positioned on an opposite edge of the connection section 152 from the cable grooves 153 (not shown). Each of the cable grooves 153 can be configured to receive poly cabling. In some embodiments, each of the cable grooves 153 can be configured to hold poly cabling (e.g., polymer cables) that is wrapped around the proximal body 104 and also around a portion of a patient's body so that the poly cabling does not move along the surface of the proximal body 104. For example, poly cabling may be wrapped around the proximal body 104 and the patient's femur, and each of the cable grooves 153 receive a portion of the poly cabling in the groove 153 to secure the poly cabling from moving along a smooth, hard and curved surface of the proximal body. While two grooves are shown in FIG. 6, some embodiments may include a single groove, where other embodiments may include three, four, five, or more cable grooves.

Figure 6:
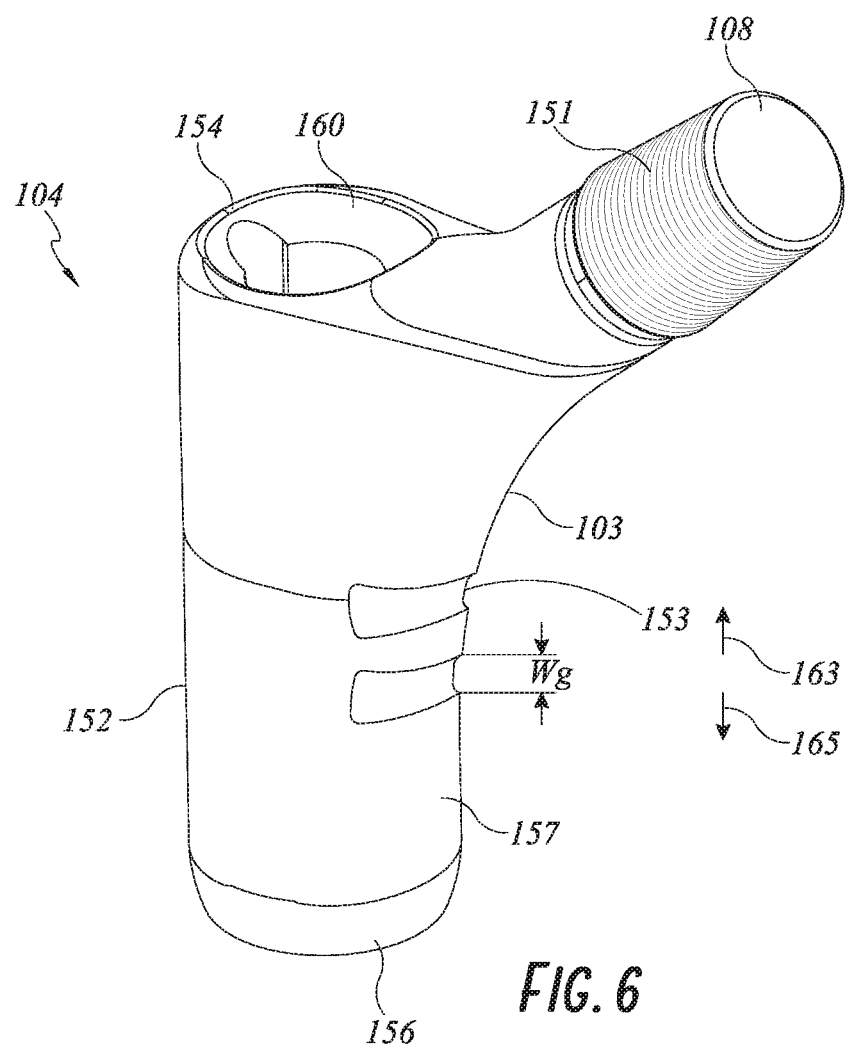
FIG. 6 depicts a front perspective view of a proximal body in accordance with an illustrative embodiment.
Figure 7:
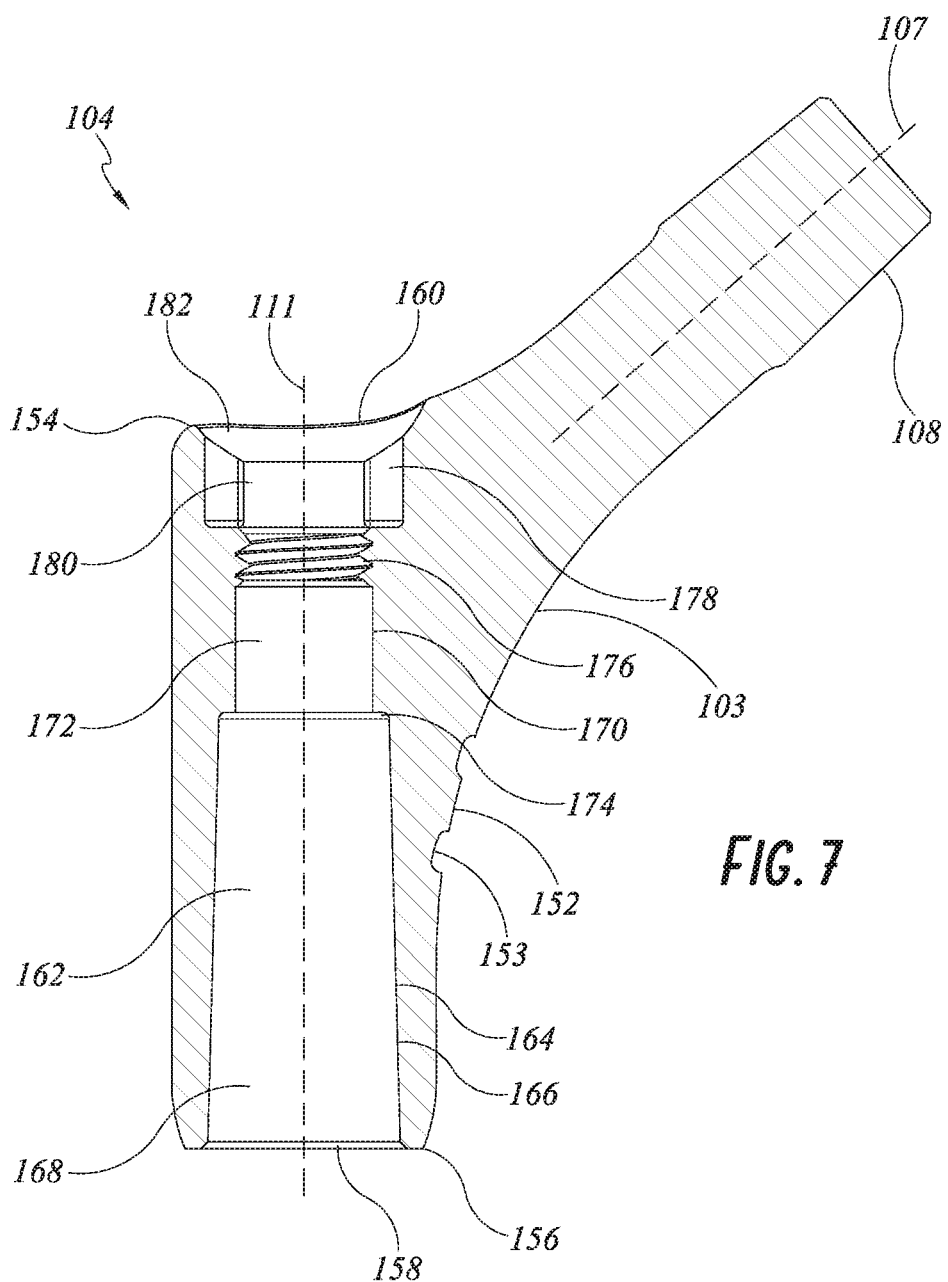
FIG. 7 depicts a cross-sectional view of a proximal body in accordance with an illustrative embodiment.
Figure 8A:
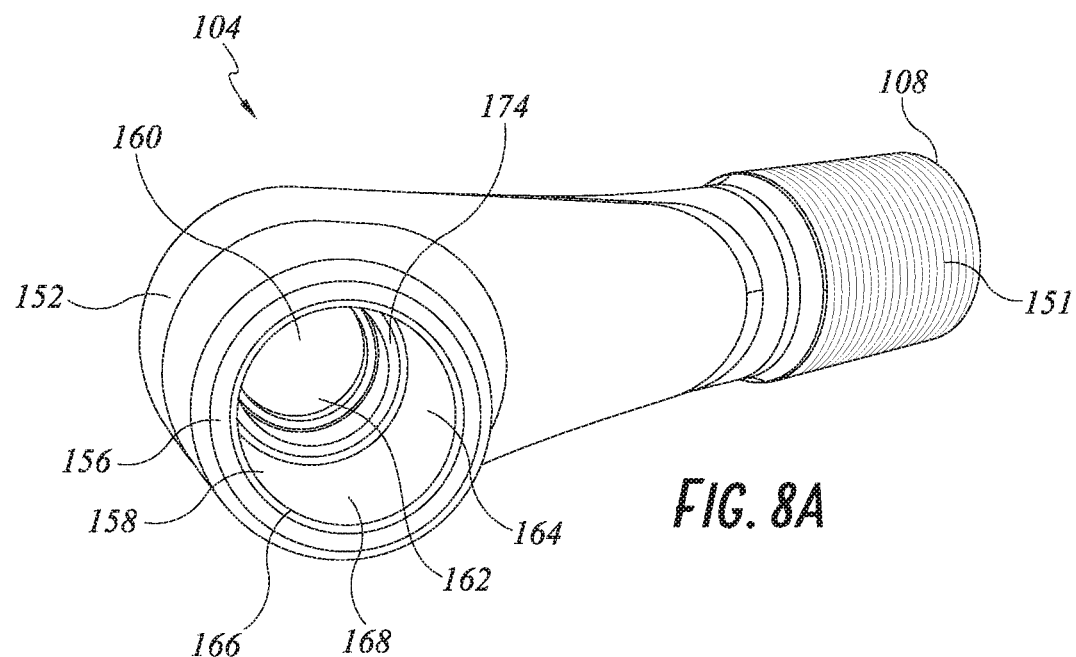
FIG. 8A depicts a bottom perspective view of a proximal body in accordance with an illustrative embodiment.
Figure 8B:
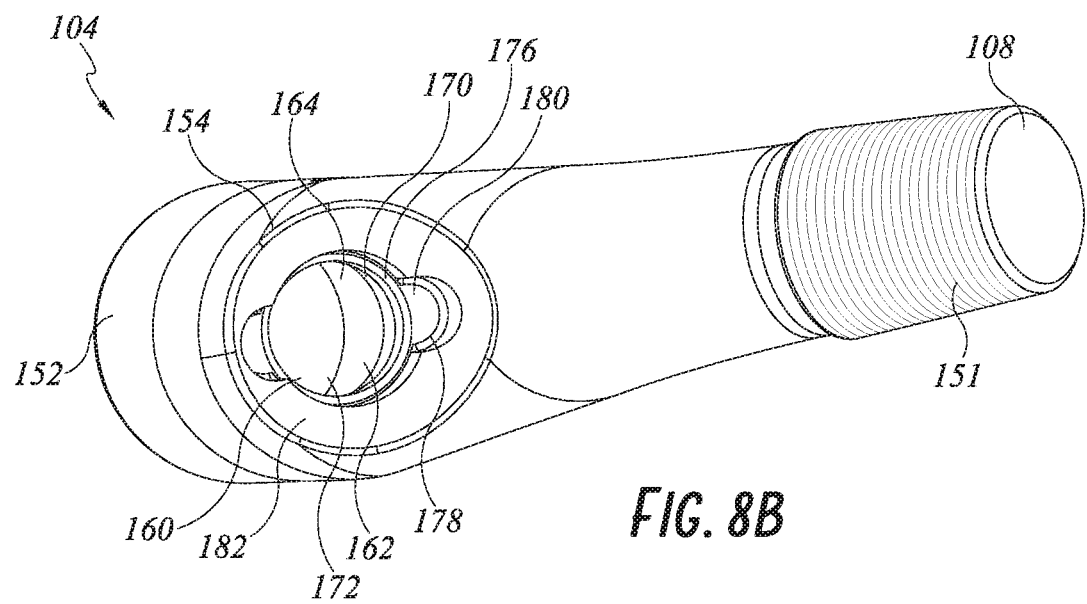
FIG. 8B depicts a top perspective view of a proximal body in accordance with an illustrative embodiment.
Figure 8C:
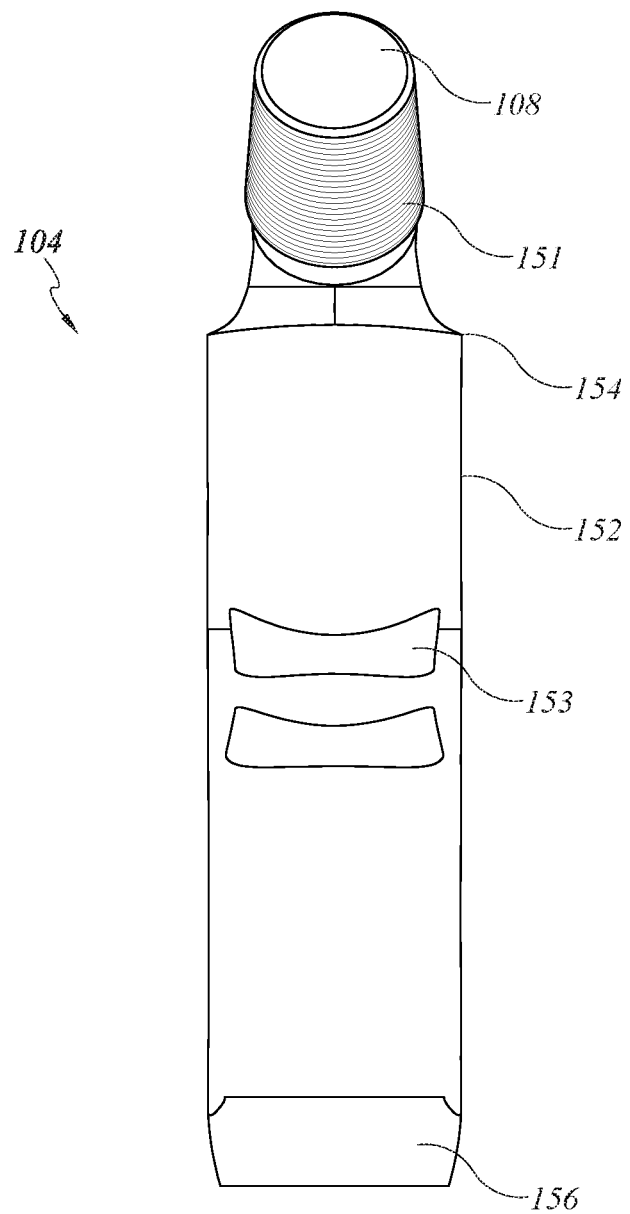
FIG. 8C depicts a side view of a proximal body in accordance with an illustrative embodiment.
Figure 8D:
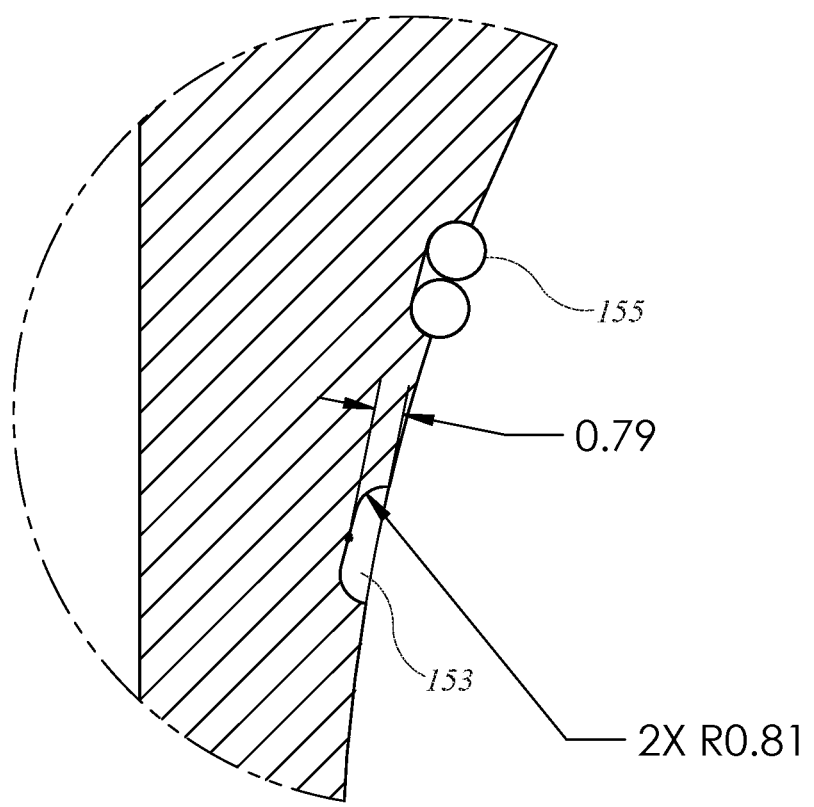
FIG. 8D depicts a cross-sectional view of a section of a proximal body in accordance with an illustrative embodiment.

In the example illustrated in FIG. 6, the cable grooves 153 are structured as an indentation (or channel) on a portion of the surface of the proximal body 104, having a selected depth and width to allow one or more cables to be placed in the cable groove. In some embodiments, the cable grooves 153 are at least 0.01 mm deep and at least 0.01 mm wide. In some embodiments, each cable groove 153 can have a different depth and width. In some embodiments, the cable grooves 153 can have a depth of 0.70 mm, 0.79 mm, or any other suitable depth. In some embodiments, the at least one groove is in the range of about 0.1 mm to 0.8 mm wide and/or about 0.1 mm to 0.8 mm deep, while in some embodiments the groves have a larger width and/or depth. In some embodiments, the grooves are normal to medial calcar surface or angles. In some embodiments, each groove is sized to receive two kinamed poly cables of 0.0625 inches in diameter (or about 1.5 mm in diameter). In some embodiments, the at least one groove is 0.20 inches deep and wide (or about 0.5 mm). In some embodiments, the second inner cavity is configured to receive the threaded body of the fastener, wherein the interior surface of the proximal body at the second inner cavity includes a threaded section configured to mate with a threaded bolt of a taper breaker. In some embodiments, the longitudinal axis of the tapered second body section is positioned at a non-zero angle to the longitudinal axis of the tapered trunnion. In various embodiments, the size of the groove may be related to the size of the cable(s) deemed necessary to use based on the implementation. In some embodiments, the size of the groove can be used for a range of diameters of cables. In some embodiments, the cable grooves 153 can have a width Wg of 0.03 inches. In some embodiments, the cable grooves 153 may have a depth of 0.03 inches. In most examples, the width Wg of each cable groove is greater than the length of the cable groove 153. In some embodiments, the cable grooves 153 are arranged normal to medial calcar surface or angles. Each cable groove 153 can be configured to receive one, two, three, four, five, or more poly cables. In some embodiments, each cable groove 153 is sized to receive two cables of about 0.0625 inches diameter. Other sized grooves are also contemplated. In various embodiment, each groove 153 a width and depth such that the function as a securing place for a cable such that the cable, when arranged to have at least a portion of the cable positioned in the groove, does not move along the proximal body 104 in a first direction 163 or a second direction 165 along the surface of the proximal body 104. The cables may be, for example, polymer cables made by Kinamed Inc., or other suitable cables. FIG. 8D depicts a sectional view of the proximal body 104 including two poly cables 155 positioned within one of the grooves 153. Each poly cable 155 may have, for example, a diameter of 0.0305 inches, 0.031 inches, 0.0315 inches, 0.062 inches, 0.0625 inches, 0.063 inches, 0.75 mm, 0.76 mm, 0.77 mm, 0.78 mm, 0.79 mm, 0.80 mm, 1.4 mm, 1.5 mm, 1.55 mm, 1.56 mm, 1.57 mm, 1.58 mm, 1.59 mm 1.6 mm, or any other suitable diameter.

In some embodiments, a length taken along the longitudinal axis 111 between the distal end 156 of the proximal body 104 and the lateral most point along the longitudinal axis 107 can be 62 mm, 72 mm, 82 mm, or any other suitable length. An offset length of the proximal body 104 includes the lateral distance between the longitudinal axis 111 of the connection portion and the lateral most point along the longitudinal axis 107 of the neck portion 108. In some embodiments, the offset length can be 40 mm, 45 mm, or any other suitable length. In some embodiments, the connection portion 104 can have a diameter of 20 mm at a section distal to the neck portion 108. In some embodiments, an angle between the longitudinal axis 111 and the longitudinal axis 107 can be 128°, 131°, or any other suitable angle.

In some embodiments, the length of the hip implant system 100 between the distal end 134b and the lateral most point of the neck portion 108 along the longitudinal axis 107 when the proximal body 104 is engaged with the distal stem 102 can be 195 mm, 205 mm, 215 mm, 235 mm, 245 mm, 255 mm, 275 mm, 285 mm, 295 mm, or any other suitable length. In some embodiments, a taper angle at the junction between the distal stem 102 and proximal body 104 can be 2°, 46', and 45". In some embodiments, a taper angle at the junction between the neck portion 108 and the femoral head 101 can be 5°, 42' 30".

Figure 9A:
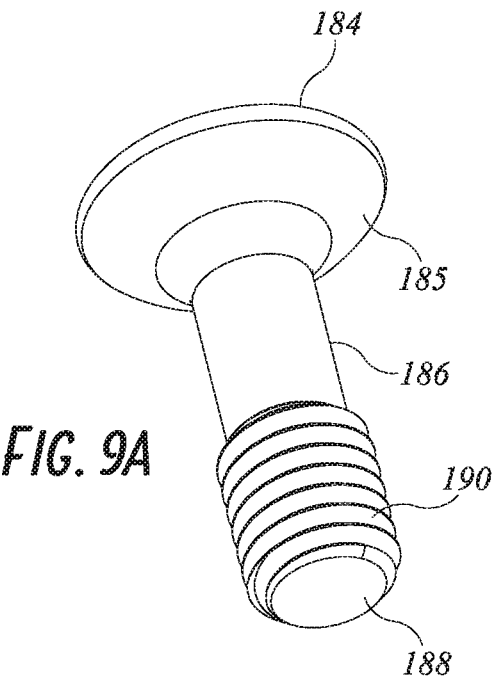
FIG. 9A depicts a perspective view of a fastener in accordance with an illustrative embodiment.
Figure 9B:
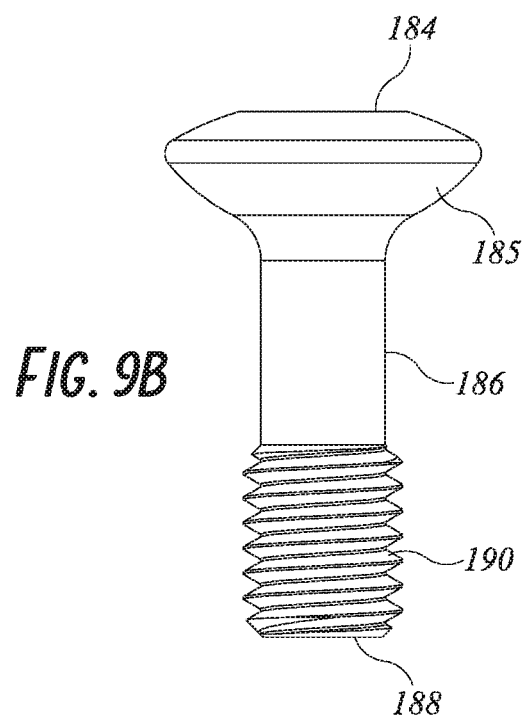
FIG. 9B depicts a front view of a fastener in accordance with an illustrative embodiment.

FIGS. 9A and 9B depict a perspective view and a front view, respectively, of the fastener 106. In some embodiments, the fastener 106 can be a locking bolt. The fastener 106 includes a head 184 and a threaded body 186. The head 184 includes a spherical portion 185 configured to engage the spherical rim 182 of the proximal body 104. The spherical portion 185 can be configured to conform to the shape of the spherical rim 182 in order restrict movement and/or provide stabilization in a lateral direction. The threaded body 186 can include distal end 188 having a threaded section 190 having one or more threads, grooves, or other surface features configured to mate with the threaded portion 126 of the interior surface 122 of the tapered trunnion 110 of the distal stem 102. In some embodiments, the head 184 of the fastener 106 can be configured to be received in the third inner cavity section 180 of the proximal body 104. At least a portion of the head 184 of the fastener 106 can have a circumference or cross-sectional area less than the circumference or cross-sectional area of the third inner cavity section 180. In some embodiments, at least a portion of the head 184 can have a circumference or cross-sectional area greater than the circumference or cross-sectional area of the second inner cavity section 172 such that spherical portion 185 of the head 184 can abut (or make contact with) the spherical rim 182 defined by the proximal end of the second interior surface section 170 of the connection portion 152 of the proximal body 104 when the fastener 106 is received within the proximal body 104. In such embodiments, the surface of the spherical portion 185 of the head 184 contacts the surface of the spherical rim 182 to provide a shaped friction surface contact that helps prevent a tightly seated fastener 106 from loosening up over time and aligns and seats the fastener 106 into the proximal body 104. In some embodiments, the threaded section 190 of the threaded body can be configured to mate with the threaded section 126 of the interior surface 122 of the tapered trunnion 110 of the distal stem 102 such that the proximal end 114 of the tapered trunnion 110 of the distal stem 102 abuts the lip 174 defined by the distal end the second interior surface section 170 and a portion of the head 184 of the fastener 106 abuts the spherical rim 182 defined by the proximal end of the second interior surface section 170. Such a configuration allows the fastener 106, proximal body 104, and distal stem 102 to be secured in place relative to one another. In some embodiments, the fastener can have a length of 65 mm, 75 mm, 85 mm, or any other suitable length.

Figure 10A:
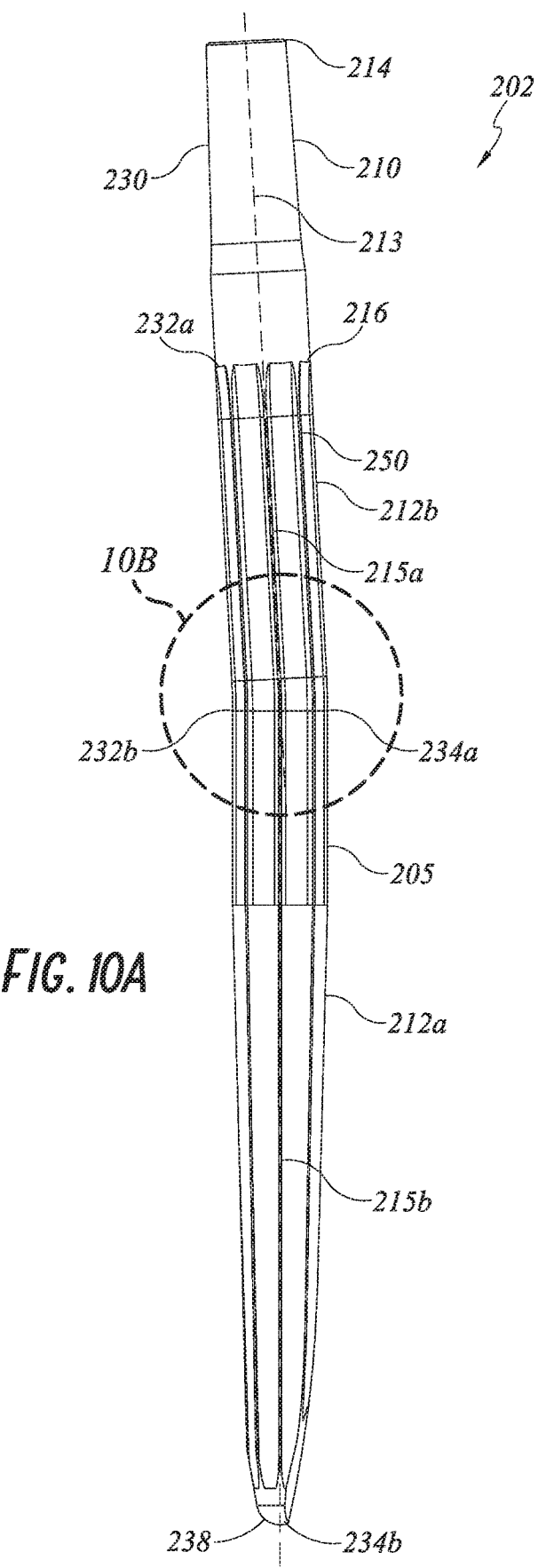
FIG. 10A depicts a side view of a distal stem in accordance with an illustrative embodiment.
Figure 10B:
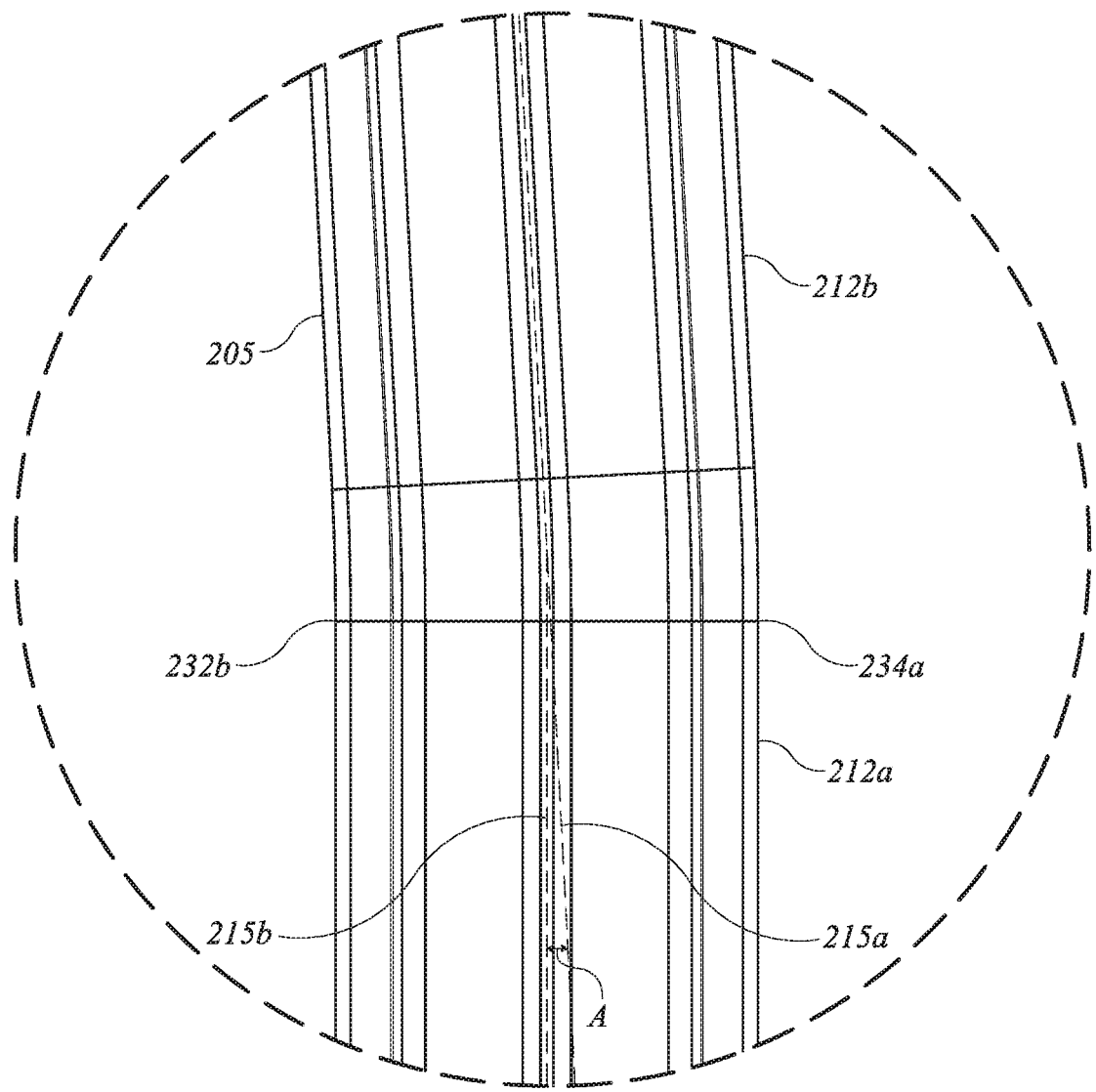
FIG. 10B depicts a sectional view of an enlarged section of a distal stem in accordance with an illustrative embodiment.

FIGS. 10A and 10B depict a side view and a sectional view, respectively, of a distal stem 202 in accordance some embodiments. The distal stem 202 can include many of the same or similar features to the distal stem 102, described with respect to FIGS. 2-5c. For example, the distal stem includes a tapered trunnion 210 having a proximal end 214, a distal end 216, and a longitudinal axis 213 (illustrated by a dashed line) extending therebetween. The tapered trunnion 210 can further include an inner cavity extending from an opening at the distal end 214 configured to receive a fastener, such as fastener 106.

The distal stem 202 further includes a stem body 205. The stem body 205 includes a first body section 212a and a section body section 212b. The second body section 212b includes a proximal end 232a, a distal end 234b, and a longitudinal axis 215a extending therebetween. The second body section 212b extends distally from the distal end 216 of the tapered trunnion 210. In the embodiment of FIGS. 10A and 10B, the longitudinal axis 215a of the second body section 212b is aligned with or generally aligned with the longitudinal axis 213 of the tapered trunnion 210.

The first body section 212a includes a proximal end 234a, a distal end 234b, and a longitudinal axis 215b (illustrated by a dashed line) extending therebetween. The first body section 212a extends distally from the distal end 232b of the second body section 212b. At least a portion of the first body section 212a is tapered such that a first circumference or cross-sectional area of the first body section 212a perpendicular to the longitudinal axis 215b of the first body section 212a is smaller than a second circumference or cross-sectional area of the first body section 212a perpendicular to the longitudinal axis 215b positioned proximal to the first circumference or cross sectional area. The first body section 212a further includes a distal tip 238. The distal tip 238 can be generally similar to the distal tip 138, described with respect to FIGS. 2-5.

As shown in FIGS. 10A and 10B, the distal stem 202 has a "bowed" configuration. For example, the longitudinal axis 215b of the first body section 212a is not exactly aligned to the longitudinal axis 215a of the second body section 212b such that the a single longitudinal axis is coincident with the longitudinal axis 215b of the first body section 212a and the longitudinal axis 215a of the second body section 212b. That is, the longitudinal axis 215b of the first body section 212a is positioned at a non-zero angle A to the longitudinal axis 215a of the second body section 212b to facilitate introduction and/or residence of the distal stem 202 into a femoral canal. The non-zero angle A can be, for example, a small angle including but not limited to 2 degrees, 3 degrees, 4 degrees, 5 degrees, or any other suitable angle. The bowed configuration of the distal stem 202 can reduce impact and/or friction on an interior surface defining the femoral canal by the distal stem 202 during introduction into or residence within the femoral canal.

The stem body 505 further includes fins 550. In various embodiments, the fins 550 can be similar, or the same, as the fins 150 described with respect to FIG. 2-5. As shown in FIGS. 10A and 10B, the fins 550 extend along the first body section 212a and the second body section 212b. However, in some embodiments, the fins may extend along only one of the first body section 212a and the second body section 212b.

In some embodiments, the stem body 205 can have a length of 120 mm, 130 mm, 170 mm, 210 mm, or any other suitable size for implantation into the femoral canal. In some embodiments, the first body section 212a can have a length of 120 mm, 130 mm, or any other suitable size.

The core diameter of stem body 205 at or near the proximal end of 234a of the first body section 212a (in some embodiments, for example, at a point 120 mm or 130 mm proximal to the distal end 234b of the first body section 212a) can be 14.5 mm, 15.5 mm, 16.0 mm. 16.5 mm, 17.0 mm, 17.5 mm, 18.0 mm, 18.5 mm, 19.0 mm, 20.0 mm, 20.5 mm, 21.0 mm, 22.0 mm, 23.0 mm, 24.0 mm, 25.0 mm, 27.0 mm or any other suitable diameter. The core diameter of stem body 205 at a point 65 mm or about 65 mm proximal to the distal end 234b can be 11.2 mm, 12.2 mm, 12.6 mm, 13.6 mm, 14.6 mm, 15.6 mm, 17.6 mm, 19.6 mm, 21.6 mm, 23.6 mm or any other suitable diameter. The core diameter at a point 11.1 mm, 12.4 mm, 13.7 mm, 15.0 mm, 16.3 mm, 17.6 mm, 18.9 mm, 21.4 mm, 24.0 mm, 26.6 mm, or 29.2 mm proximal to the distal end 234b of the first body section 212a can be 7.9 mm, 9.0 mm, 9.0 mm, 11.0 mm, 12.1 mm, 13.2 mm, 15.3 mm, 17.5 mm, 19.6 mm, 21.7 mm, or any other suitable diameter. In some embodiments, the first body section 212a tapers at a 3° angle from the proximal end 134a to the distal end 134b of the first body section 212a.

Figure 11:
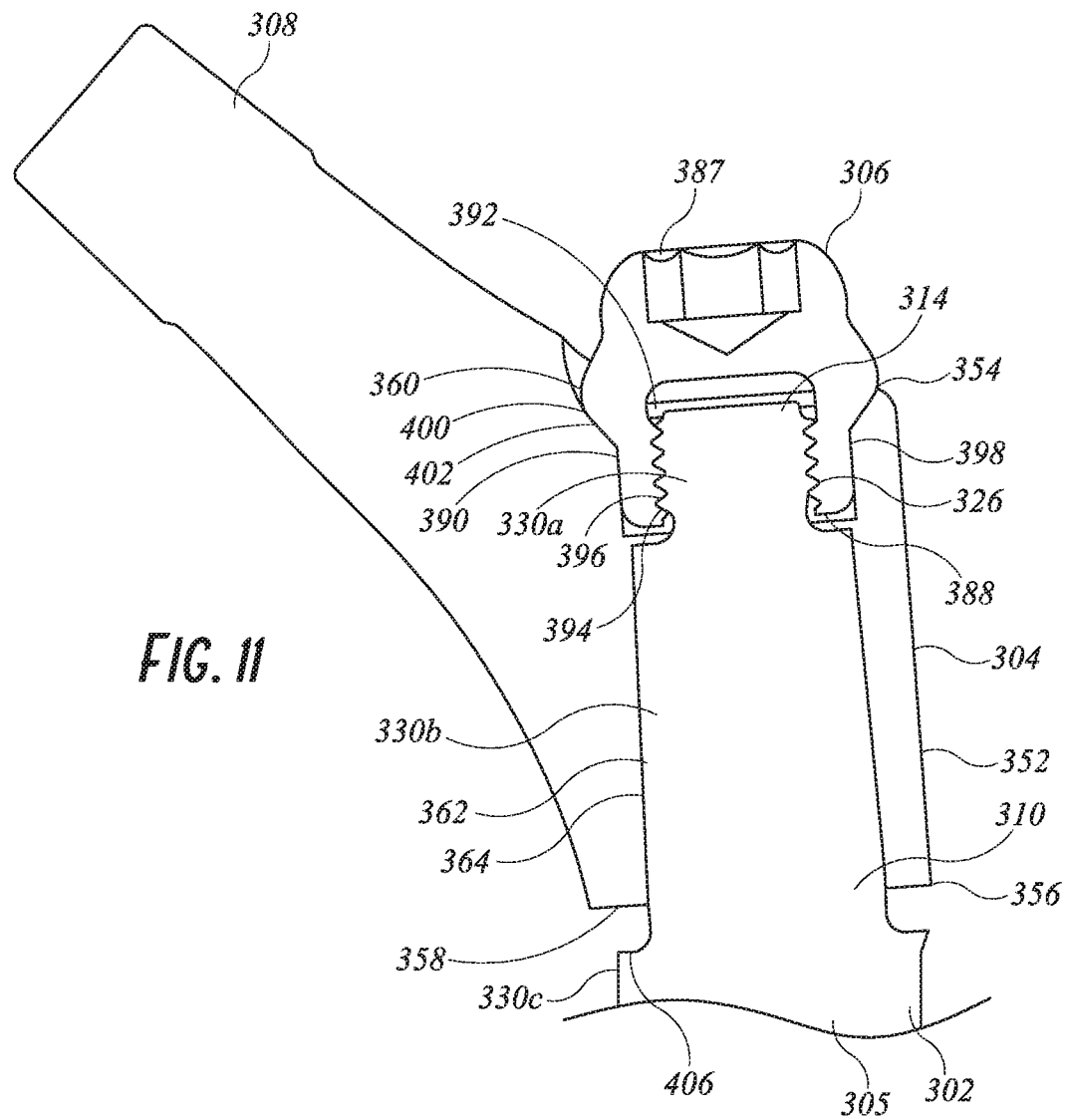
FIG. 11 depicts a cross-sectional view of a section of a hip implant system in accordance with an illustrative embodiment.

FIG. 11 depicts a cross-sectional view of a section of a hip implant system 300 in accordance with some embodiments. The hip implant system 300 includes a proximal body 304, distal stem 302, and a fastener 306. The distal stem 302 can include many of the same or similar features to the distal stems 102 and 202. FIG. 11 shows a portion of a tapered trunnion 310 of the distal stem 302 having a proximal end 314, a distal end (not show), and a longitudinal axis extending therebetween. The tapered trunnion 310 includes a first exterior surface portion 330A extending from the proximal end 314 of the tapered trunnion 310 and a second exterior surface portion 330B, immediately distal to the first exterior surface portion 330A. The first exterior surface portion 330A includes a threaded section 326 configured to mate with a complementary threaded section of the fastener 306. The second exterior surface section 330B can have a circumference greater than that of the first exterior surface section 330A.

The distal stem 302 further includes a stem body 305 having a third exterior surface portion 330C extending distally from the second exterior surface portion 330B, the third exterior surface portion 330C having a circumference or cross-sectional area greater than that of the second exterior surface portion 330B, such that a proximal end of the third exterior surface portion 330C defines a lip 406.

The proximal body 304 includes a connection portion 352 and a neck portion 308. The connection portion 352 includes a proximal end 354 and a distal end 356. The distal end 356 of the connection portion 352 can be configured to engage the proximal end 314 of the tapered trunnion 310 of the distal stem 302. The distal end 356 of the connection portion 352 includes a first opening 358 configured to receive the proximal end 314 of the tapered trunnion 310. The connection portion 352 further includes a second opening 360 at the proximal end 354 of the connection portion 352. The second opening 360 can be configured to receive the fastener 306.

The connection portion 352 of the proximal body 304 further include an inner cavity 362 extending between the first opening 358 and the second opening 360. The inner cavity 362 is defined by an interior surface 364 of the connection section 352.

The inner cavity 362 is configured to receive the first exterior surface portion 330A and at least a portion of the second exterior surface portion 330B of the tapered trunnion 310. The circumference or cross-sectional area of the second exterior surface portion 330B of the tapered trunnion 310 can be less than that of the circumference or cross-sectional area of the inner cavity 362. In some embodiments, the interior surface 364 of the proximal body 304 can be configured to form an interference fit with the second exterior surface portion of the tapered trunnion 310.

The second opening 360 of the connection portion 352 of the proximal body 304 can be configured to receive a portion of the fastener 306. The fastener 306 includes a proximal end 387 and a distal end 388. The fastener 306 further includes a mating portion 390. The mating portion 390 includes an inner cavity 392 defined by an interior surface 394 of the mating portion 390. The inner cavity 392 can extend from the distal end 388 of the fastener 306 at least partially toward the proximal end 387 of the fastener 306. The interior surface 394 of the mating portion 390 further includes a threaded section 396 configured to mate with the threaded section 326 of the first exterior surface portion 330A of the tapered trunnion 310 of the distal stem 302. An exterior surface 398 of the mating portion 390 of the fastener 306 can have a circumference or cross-sectional area less than the circumference or cross sectional area of the inner cavity 392, such that the mating portion 390 of the fastener 306 can be received within the inner cavity 362 of the proximal body 304.

The fastener 306 further includes an inclined contact face 400 positioned proximal the mating portion 390. The inclined contact face 400 can extend proximally and laterally from the mating portion 390 such that the circumference of at least a portion of the inclined contact face 400 is greater than the circumference of the exterior surface 398 of the mating portion 390. The proximal end 354 of the connection portion 352 of the proximal body 304 also includes an inclined mating surface 402 configured to receive the inclined mating surface 400 of the fastener 306. The inclined mating surface 402 of the proximal body 304 has a circumference greater than the circumference of the interior surface 394 of the proximal body 304 immediately distal the inclined mating surface 402. This configuration allows the inclined mating surface 400 of the fastener 306 to abut the inclined mating surface 402 of the proximal body 304 when the threaded section 396 of the mating portion 390 of the fastener 306 is tightened to the threaded section 326 of first exterior surface portion 330A of the tapered trunnion 310 of the distal stem 302.

In some embodiments, the third exterior surface portion 330C of the tapered trunnion 310 of the distal stem 302 can have a circumference or cross-sectional area greater than that of the interior surface 394 of the proximal body 304, such that the lip 406 is configured to abut the distal end 356 of the proximal body 304 when the threaded section 396 of the mating portion 390 of the fastener 306 is tightened to the threaded section 326 of first exterior surface portion 330A of the tapered trunnion 310 of the distal stem 302.

Figure 12:
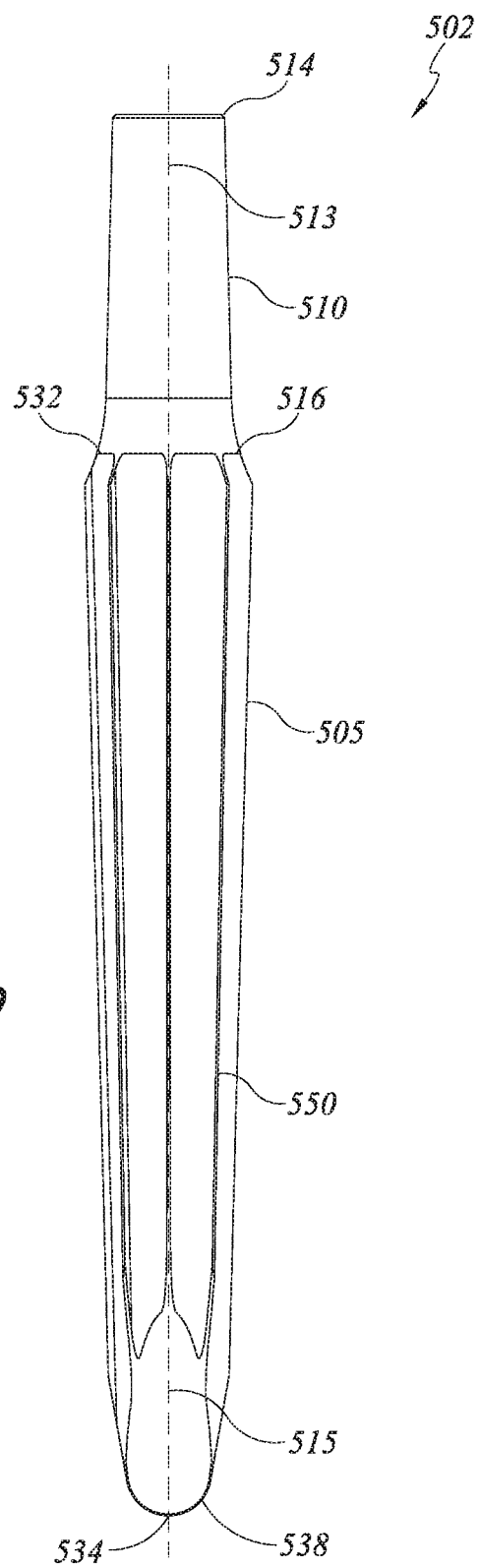
FIG. 12 depicts front view of a distal stem in accordance with an illustrative embodiment.

FIG. 12 depicts a distal stem 502 in accordance some embodiments. The distal stem 502 can include many of the same or similar features to the distal stems 102, 202, and 302, described with respect to FIGS. 2-5 and 10A-11. For example, the distal stem includes a tapered trunnion 510 having a proximal end 514, a distal end 516, and a longitudinal axis 513 (illustrated as a dotted line) extending therebetween. The tapered trunnion 510 can further include an inner cavity extending from an opening at the distal end 514 configured to receive a fastener, such as fastener 106.

The distal stem 502 further includes a stem body 505. The stem body 505 includes a proximal end 532, a distal end 534, and a longitudinal axis 515 extending therebetween. The stem body 505 extends distally from the distal end 516 of the tapered trunnion 510. In the embodiment of FIG. 12, the longitudinal axis 515 of the stem body 505 is aligned with or generally aligned with the longitudinal axis 513 of the tapered trunnion 510.

At least a portion of the stem body 505 is tapered such that a first circumference or cross-sectional area of the stem body 505 perpendicular to the longitudinal axis 515 of the stem body 505 is smaller than a second circumference or cross-sectional area of the first body section 512 perpendicular to the longitudinal axis 515 positioned proximal to the first circumference or cross sectional area. The stem body 505 further includes a distal tip 538. In various embodiments, the distal tip 538 can be similar, or the same, as the distal tip 138 described with respect to FIGS. 2-5. The stem body 505 further includes fins 550. In various embodiments, the fins 550 can be similar, or the same, as the fins 150 described with respect to FIG. 2-5.

In some embodiments, the stem body 505 can have a length of 120 mm, 130 mm, 170 mm, 210 mm, or any other suitable size for implantation into the femoral canal.

The core diameter of stem body 505 at or near the proximal end 532 of the stem body 505 (in some embodiments, for example, at a point 120 mm or 130 mm proximal to the distal end 534 of the stem body 505) can be 14.5 mm, 15.5 mm, 16.0 mm. 16.5 mm, 17.0 mm, 17.5 mm, 18.0 mm, 18.5 mm, 19.0 mm, 20.0 mm, 20.5 mm, 21.0 mm, 22.0 mm, 23.0 mm, 24.0 mm, 25.0 mm, 27.0 mm or any other suitable diameter. The core diameter of stem body 505 at a point 65 mm or about 65 mm proximal to the distal end 534 can be 11.2 mm, 12.2 mm, 12.6 mm, 13.6 mm, 14.6 mm, 15.6 mm, 17.6 mm, 19.6 mm, 21.6 mm, 23.6 mm or any other suitable diameter. The core diameter at a point 11.1 mm, 12.4 mm, 13.7 mm, 15.0 mm, 16.3 mm, 17.6 mm, 18.9 mm, 21.4 mm, 24.0 mm, 26.6 mm, or 29.2 mm proximal to the distal end 234b of the first body section 212a can be 7.9 mm, 9.0 mm, 9.0 mm, 11.0 mm, 12.1 mm, 13.2 mm, 15.3 mm, 17.5 mm, 19.6 mm, 21.7 mm, or any other suitable diameter. In some embodiments, the stem body 505 tapers at a 3° angle from the proximal end 534 to the distal end 534 of the first body section 505.

Figure 13C:
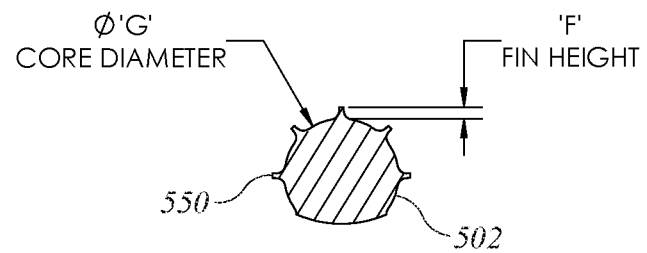
FIG. 13C depicts a cross-sectional view of a distal stem in accordance with an illustrative embodiment.
Figure 13D:
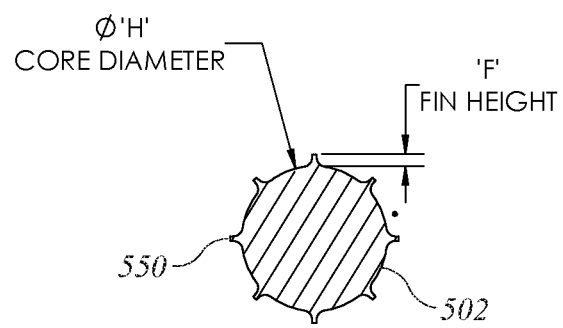
FIG. 13D depicts a cross-sectional view of a distal stem in accordance with an illustrative embodiment.
Figure 13E:
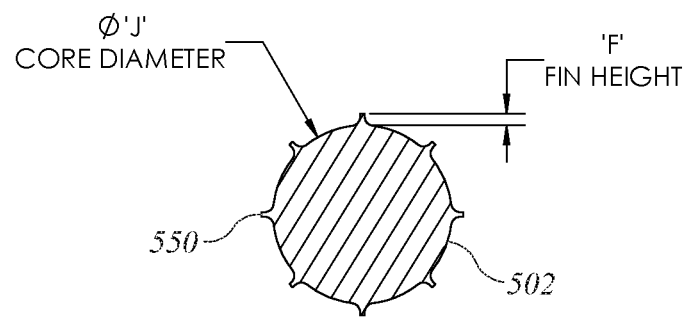
FIG. 13E depicts a cross-sectional view of a distal stem in accordance with an illustrative embodiment.

FIGS. 13A-B depict a hip implant system 500 including an embodiment of the proximal body 104 and an embodiment of the distal stem 502. FIGS. 13C-E depict cross-sectional views of the embodiment of the distal stem 502 depicted in FIGS. 13A-B showing fins 550. FIG. 13C depicts a cross-section of the distal stem 502 taken along line 13C-13C of FIG. 13A. FIG. 13D depicts a cross-section of the distal stem 502 taken along line 13D-13D of FIG. 13A. FIG. 13E depicts a cross-section of the distal stem 502 taken along line 13E-13E of FIG. 13A. Tables 1 and 2 provide example values of a length A of the proximal body 104, an Offset B of the proximal body 104, a Total Length C of the implant system 500, an angle D between the longitudinal axis of the connection portion of the proximal body 104 and the longitudinal axis of the neck portion of the proximal body 104, a length E of a section of the distal stem 502, a diameter K of a section of the tapered trunnion of the distal stem 502, a length L of a section of the distal stem 102, a core diameter G of the distal stem 502 along line 13C-13C, a fin height F of the distal stem 502 along line 13C-13C, a core diameter H of the distal stem 502 along line 13D-13D, a fin height F of the distal stem 502 along line 13D-13D, a core diameter J of the distal stem 502 along line 13E-13E, a fin height F of the distal stem 502 along line 13E-13E, as shown in FIGS. 13A-E. The length E represents a segment of the distal stem 502 that tapers towards the distal end 534 of the distal stem 502 at a greater angle than the taper of the segment of the distal stem 502 proximal to the segment represented by the length E. In other words, in this embodiment, along the length of the distal stem 502 from the line 13E-13E to the line 13C-13C there is a first amount (or angle) of taper where the core diameter of the distal stem 502 (at least in one cross-sectional direction) is decreasing at a first rate (e.g., as a function of distance along the distal stem 502). Further, along the length of the distal stem 502 from line 13C-13C to the distal end of the distal stem 502 the core diameter of the of the distal stem 502 (at least in one cross-sectional direction) decreases at a second rate (e.g., as a function of distance along the length of the distal stem 502 from line 13C-13C to the distal stem), such that there is two different tapers along the length E of the distal stem 502. Other examples may also have more than one taper amount along the distal stem, for example, as illustrated in FIGS. 14, 15 and 16.

TABLE 1

| PROXIMAL BODY | OFFSET | 'A' (mm) | 'B' (mm) | 'C' (mm) | 'D' (deg) |
|---|---|---|---|---|---|
| 65 | STD | 62 | 40 | 195 | 131 |
|  | LAT |  | 45 |  | 128 |
| 75 | STD | 72 | 40 | 205 | 131 |
|  | LAT |  | 45 |  | 128 |
| 85 | STD | 82 | 40 | 215 | 131 |
|  | LAT |  | 45 |  | 128 |

TABLE 2

| Stem Size | 'E' [mm] | 'F' [mm] | 'G' [mm] | 'H' [mm] | 'J' [mm] | 'K' [mm] | 'L' [mm] |
|---|---|---|---|---|---|---|---|
| 16 × 130 | 13.7 | 1.0 | 9.9 | 12.6 | 15.5 | 18.0 | 38.1 |
| 17 × 130 | 15.0 | 1.0 | 11.0 | 13.6 | 16.5 | 19.0 | 38.1 |
| 18 × 130 | 16.3 | 1.5 | 11.0 | 13.6 | 16.5 | 20.0 | 50.8 |
| 19 × 130 | 17.6 | 1.5 | 12.1 | 14.6 | 17.5 | 21.0 | 50.8 |
| 20 × 130 | 18.9 | 1.5 | 13.2 | 15.6 | 18.5 | 22.0 | 50.8 |
| 22 × 130 | 21.4 | 1.5 | 15.3 | 17.6 | 20.5 | 24.0 | 50.8 |

Figure 14A:
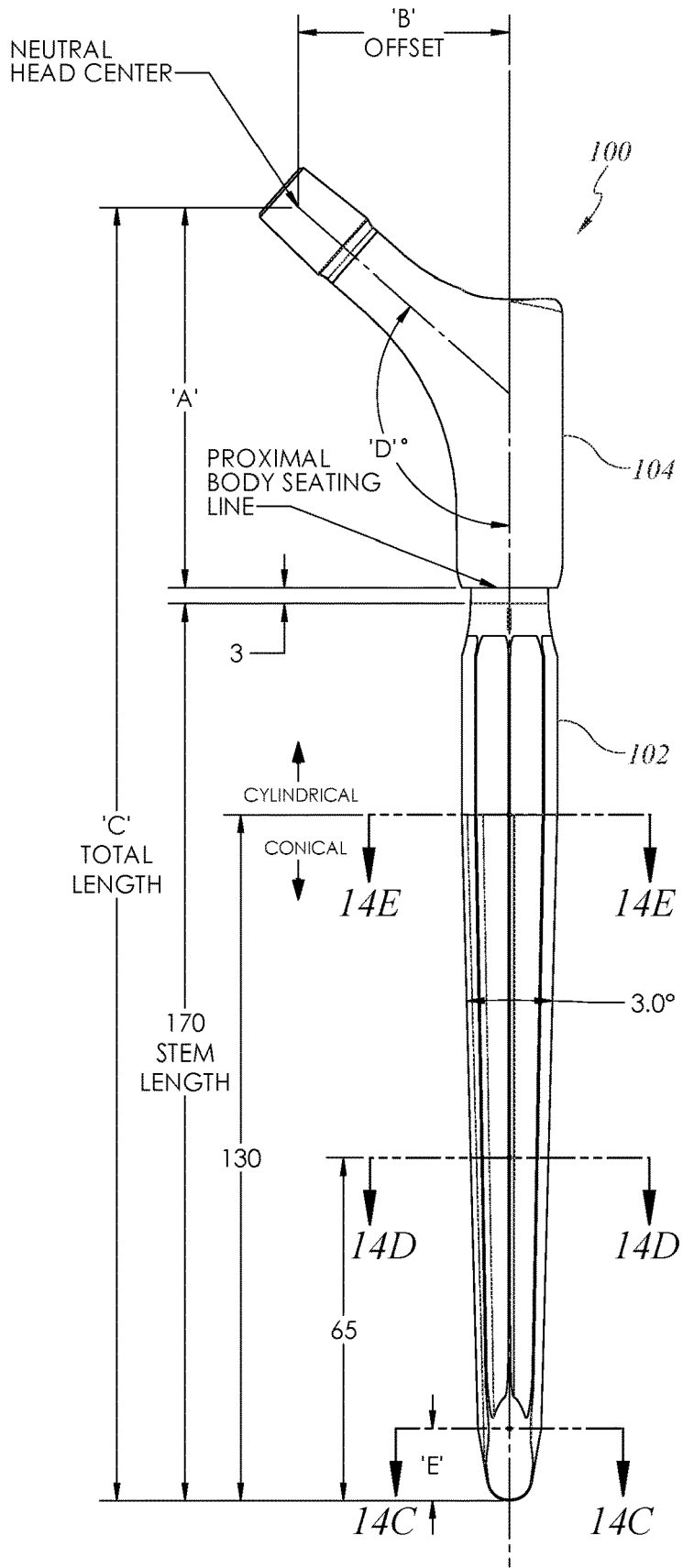
FIG. 14A depicts a front view a hip implant system in accordance with an illustrative embodiment.
Figure 14B:
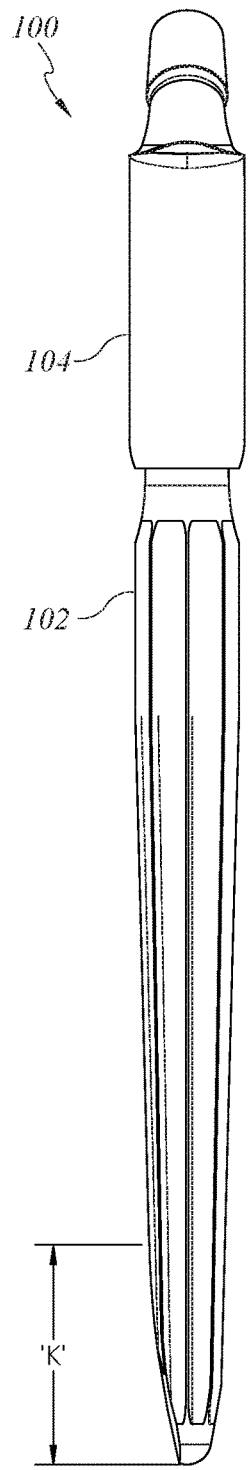
FIG. 14B depicts a side view of a hip implant system in accordance with an illustrative embodiment.
Figure 14C:
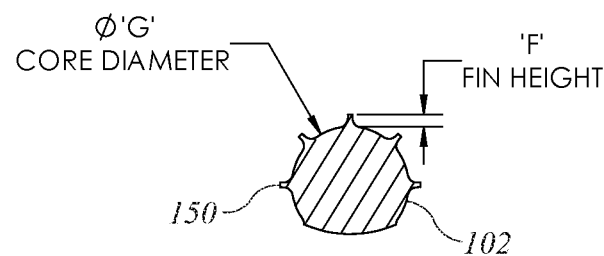
FIG. 14C depicts a cross-sectional view of a distal stem in accordance with an illustrative embodiment.
Figure 14D:
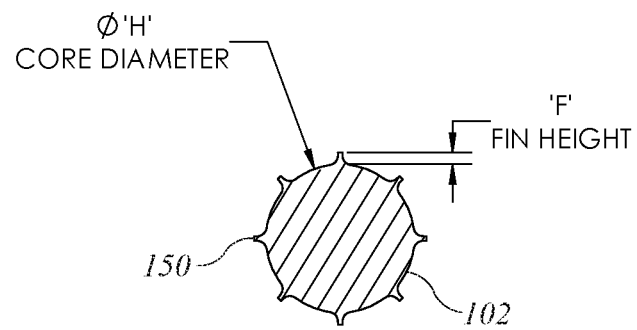
FIG. 14D depicts a cross-sectional view of a distal stem in accordance with an illustrative embodiment.
Figure 14E:
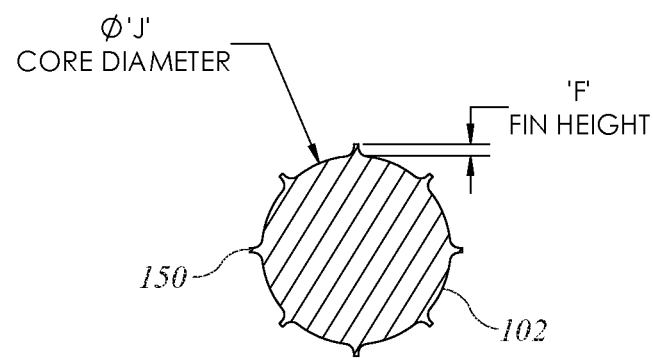
FIG. 14E depicts a cross-sectional view of a distal stem in accordance with an illustrative embodiment.

FIGS. 14A-B depict an example of a hip implant system 100 including an embodiment of the proximal body 104 and an embodiment of the distal stem 102. FIGS. 14A-B do not show the femoral head 101 of the hip implant system 100. FIGS. 14C-E depict cross-sectional views of the embodiment of the distal stem 102 depicted in FIGS. 14A-B showing fins 150. FIG. 14C depicts a cross-section of the distal stem 102 taken along line 14C-14C of FIG. 14A. FIG. 14D depicts a cross-section of the distal stem 102 taken along line 14D-14D of FIG. 14A. FIG. 14E depicts a cross-section of the distal stem 102 taken along line 14E-14E of FIG. 14A. Tables 3 and 4 provide example values of a length A of the proximal body 104, an Offset B of the proximal body 104, a Total Length C of the proximal body 104 and the distal stem 102 of the implant system 100, an angle D between the longitudinal axis of the connection portion of the proximal body 104 and the longitudinal axis of the neck portion of the proximal body 104, a length E of a section of the distal stem 102, a length K of a section of the distal stem 102, a core diameter G of the distal stem 102 along line 14C-14C, a fin height F of the distal stem 102 along line 14C-14C, a core diameter H of the distal stem 102 along line 14D-14D, a fin height F of the distal stem 102 along line 14D-14D, a core diameter J of the distal stem 102 along line 14E-14E, a fin height F of the distal stem 102 along line 14E-14E, as shown in FIGS. 14A-E. The length E represents a segment of the distal stem 102 that tapers towards the distal end of the distal stem 102 at a greater angle than the segment of the distal stem 102 proximal to the segment represented by the length E.

TABLE 3

| PROXIMAL BODY | OFFSET | 'A' (mm) | 'B' (mm) | 'C' (mm) | 'D' (deg) |
|---|---|---|---|---|---|
| 65 | STD | 62 | 40 | 235 | 131 |
|  | LAT |  | 45 |  | 128 |
| 75 | STD | 72 | 40 | 245 | 131 |
|  | LAT |  | 45 |  | 128 |
| 85 | STD | 82 | 40 | 255 | 131 |
|  | LAT |  | 45 |  | 128 |

TABLE 4

| Stem Size | 'E' [mm] | 'F' [mm] | 'G' [mm] | 'H' [mm] | 'J' [mm] | 'K' [mm] |
|---|---|---|---|---|---|---|
| 16 × 170 | 13.7 | 1.0 | 9.9 | 12.1 | 16.0 | 38.1 |
| 17 × 170 | 15.0 | 1.0 | 11.0 | 13.6 | 17.0 | 38.1 |
| 18 × 170 | 16.3 | 1.5 | 11.0 | 13.6 | 17.0 | 50.8 |
| 19 × 170 | 17.6 | 1.5 | 12.1 | 14.6 | 18.0 | 50.8 |
| 20 × 170 | 18.9 | 1.5 | 13.2 | 15.6 | 19.0 | 50.8 |
| 22 × 170 | 21.4 | 1.5 | 15.3 | 17.6 | 21.0 | 50.8 |
| 24 × 170 | 24.0 | 1.5 | 17.5 | 19.6 | 23.0 | 50.8 |
| 26 × 170 | 26.6 | 1.5 | 19.6 | 21.6 | 25.0 | 50.8 |
| 28 × 170 | 29.2 | 1.5 | 21.7 | 23.6 | 27.0 | 50.8 |

Figure 15C:
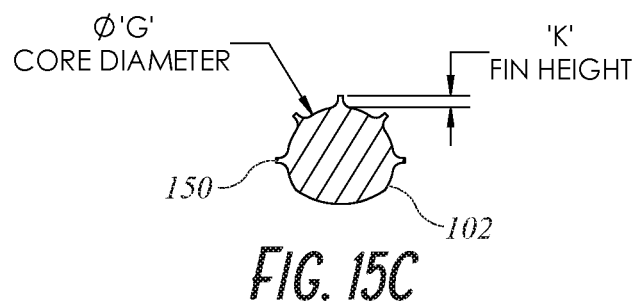
FIG. 15C depicts a cross-sectional view of a distal stem in accordance with an illustrative embodiment.
Figure 15D:
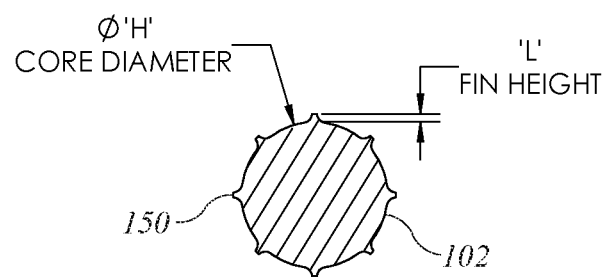
FIG. 15D depicts a cross-sectional view of a distal stem in accordance with an illustrative embodiment.
Figure 15E:
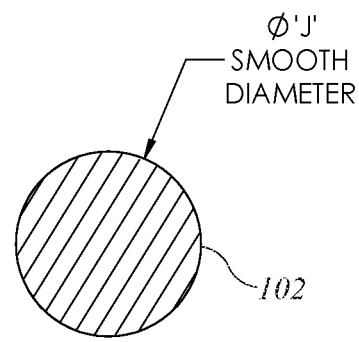
FIG. 15E depicts a cross-sectional view of a distal stem in accordance with an illustrative embodiment.

FIGS. 15A-B depict an example of a hip implant system 100 including an embodiment of the proximal body 104 and an embodiment of the distal stem 102. FIGS. 15A-B do not show the femoral head 101 of the hip implant system 100. FIGS. 15C-E depict cross-sectional views of the embodiment of the distal stem 102 depicted in FIGS. 15A-B showing fins 150. FIG. 15C depicts a cross-section of the distal stem 102 taken along line 15C-15C of FIG. 15A. FIG. 15D depicts a cross-section of the distal stem 102 taken along line 15D-15D of FIG. 15A. FIG. 15E depicts a cross-section of the distal stem 102 taken along line 15E-15E of FIG. 15A. Tables 5 and 6 provide example values of a length A of the proximal body 104, an Offset B of the proximal body 104, an angle C between the longitudinal axis of the connection portion of the proximal body 104 and the longitudinal axis of the neck portion of the proximal body 104, a stem length D of the distal stem 102, a total length E of the proximal body 104 and distal stem 102 of the implant system 100, a length F of a section of the distal stem 102, a length M of a section of the distal stem 102, a core diameter G of the distal stem 102 along line 15C-15C, a fin height K of the distal stem 102 along line 15C-15C, a core diameter H of the distal stem 102 along line 15D-15D, a fin height L of the distal stem 102 along line 15D-15D, a core diameter J of the distal stem 102 along line 15E-15E as shown in FIGS. 15A-E. As shown in Table 5, the height of the fins 150 can decrease from the distal end of the distal stem 102 towards the proximal end of the distal stem 102. The length F represents a segment of the distal stem 102 that tapers towards the distal end of the distal stem 102 at a greater angle than the segment of the distal stem 102 proximal to the segment represented by the length E.

TABLE 5

| Stem Size | 'F' [mm] | 'G' [mm] | 'H' [mm] | 'J' [mm] | 'K' [mm] | 'L' [mm] | 'M' [mm] |
|---|---|---|---|---|---|---|---|
| 14 × 130 | 11.1 | 7.9 | 11.2 | 14.5 | 0.95 | 0.68 | 38.1 |
| 14 × 170 |  |  |  |  |  |  |  |
| 14 × 210 |  |  |  |  |  |  |  |
| 15 × 130 | 12.4 | 9.0 | 12.2 | 15.5 |  |  |  |
| 15 × 170 |  |  |  |  |  |  |  |
| 15 × 210 |  |  |  |  |  |  |  |

TABLE 6

| PROXIMAL BODY | OFFSET | 'A' [mm] | 'B' [mm] | 'C' [DEG] | 'D' [mm] 130 STEM | 'D' [mm] 170 STEM | 'D' [mm] 210 STEM | 'E' (STEM + BODY) [mm] | | |
|---|---|---|---|---|---|---|---|---|---|---|
| 65 | STD | 62 | 40 | 128 | 130 | 170 | 210 | 195 | 235 | 275 |
|  | LAT |  | 45 | 131 |  |  |  |  |  |  |
| 75 | STD | 72 | 40 | 128 | 130 | 170 | 210 | 205 | 245 | 285 |
|  | LAT |  | 45 | 131 |  |  |  |  |  |  |
| 85 | STD | 82 | 40 | 128 | 130 | 170 | 210 | 215 | 255 | 295 |
|  | LAT |  | 45 | 131 |  |  |  |  |  |  |

Figure 16A:
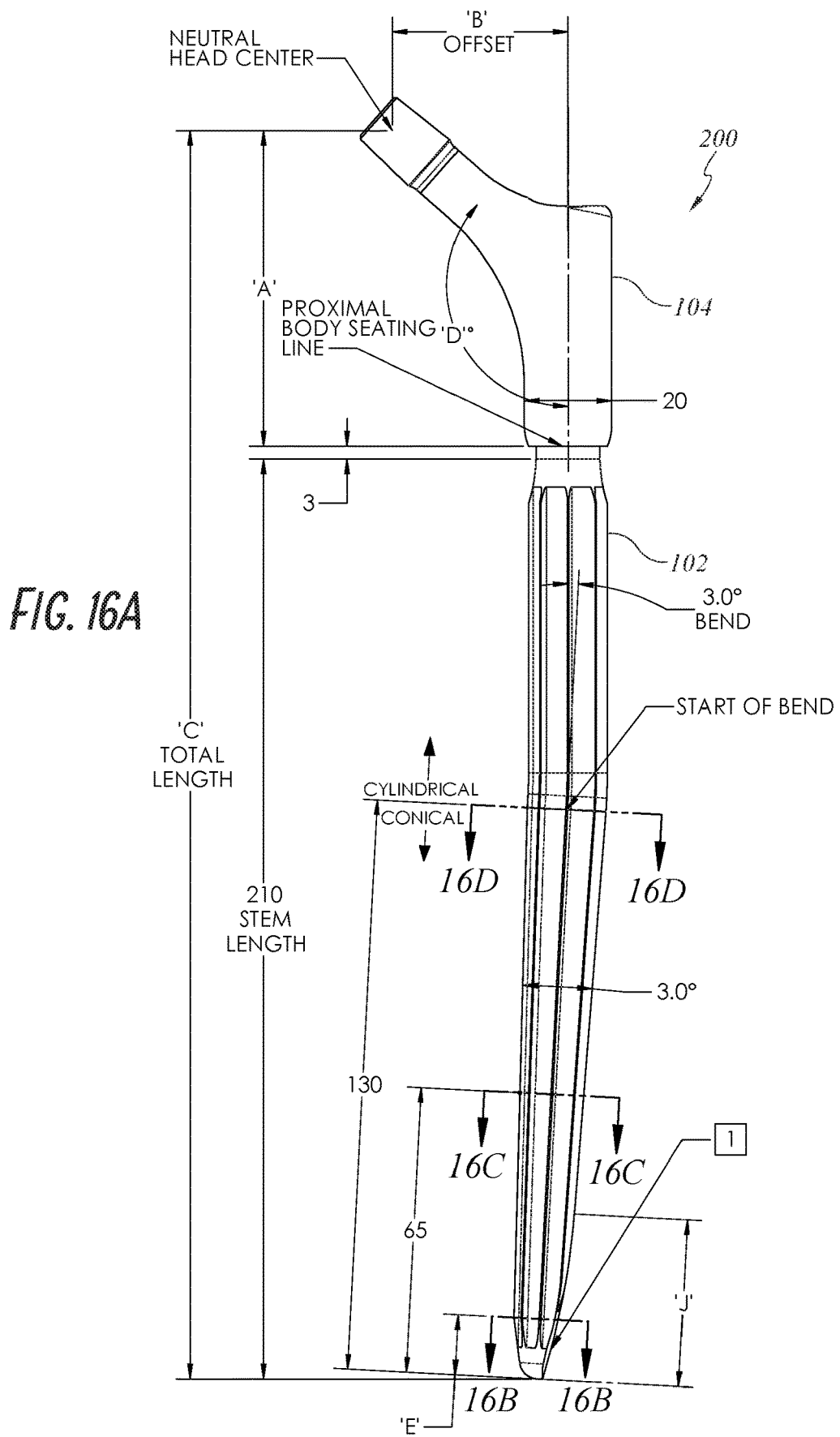
FIG. 16A depicts a front view a hip implant system in accordance with an illustrative embodiment.
Figure 16B:
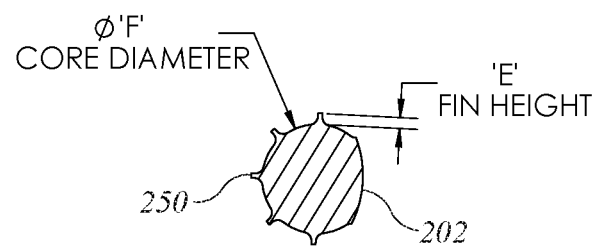
FIG. 16B depicts a cross-sectional view of a distal stem in accordance with an illustrative embodiment.
Figure 16C:
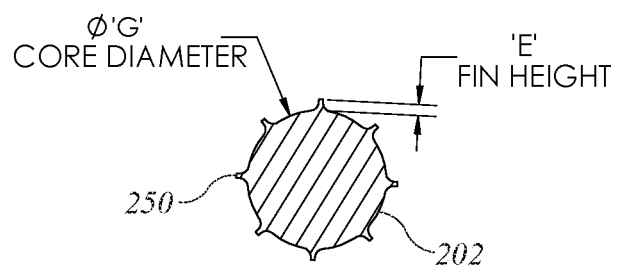
FIG. 16C depicts a cross-sectional view of a distal stem in accordance with an illustrative embodiment.
Figure 16D:
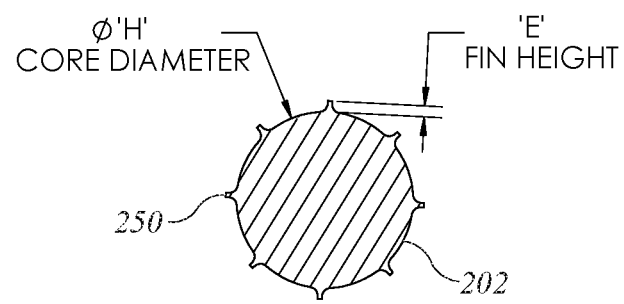
FIG. 16D depicts a cross-sectional view of a distal stem in accordance with an illustrative embodiment.

FIG. 16A depicts an example of a hip implant system 200 including an embodiment of the proximal body 104 and an embodiment of the distal stem 202. FIGS. 16B-D depict cross-sectional views of the embodiment of the distal stem 202 depicted in FIG. 16A showing fins 250. FIG. 16B depicts a cross-section of the distal stem 202 taken along line 16B-16B of FIG. 16A. FIG. 16C depicts a cross-section of the distal stem 202 taken along line 16C-16C of FIG. 16A. FIG. 16D depicts a cross-section of the distal stem 202 taken along line 16D-16D of FIG. 14A. Tables 7 and 8 provide example values of a length A of the proximal body 104, an Offset B of the proximal body 104, a Total Length C of the implant system 200, an angle D between the longitudinal axis of the connection portion of the proximal body 104 and the longitudinal axis of the neck portion of the proximal body 104, a length K of a section of the distal stem 202, a core diameter F of the distal stem 202 along line 16B-16B, a fin height E of the distal stem 202 along line 16B-16B, a core diameter G of the distal stem 202 along line 16C-16C, a fin height E of the distal stem 202 along line 16C-16C, a core diameter H of the distal stem 202 along line 16D-16D, a fin height E of the distal stem 202 along line 16D-16D, as shown in FIGS. 16A-D. The length K represents a segment of the distal stem 202 that tapers towards the distal end of the distal stem 202 at a greater angle than the segment of the distal stem 202 proximal to the segment represented by the length K.

TABLE 7

| PROXIMAL BODY | OFFSET | 'A' (mm) | 'B' (mm) | 'C' (mm) | 'D' (deg) |
|---|---|---|---|---|---|
| 65 | STD | 62 | 40 | 275 | 131 |
|  | LAT |  | 45 |  | 128 |
| 75 | STD | 72 | 40 | 285 | 131 |
|  | LAT |  | 45 |  | 128 |
| 85 | STD | 82 | 40 | 295 | 131 |
|  | LAT |  | 45 |  | 128 |

TABLE 8

| Stem Size | 'K' [mm] | 'E' [mm] | 'F' [mm] | 'G' [mm] | 'H' [mm] | 'F' [mm] |
|---|---|---|---|---|---|---|
| 16 × 210 | 13.7 | 1.0 | 9.9 | 12.6 | 16.0 | 38.1 |
| 17 × 210 | 15.0 | 1.0 | 11.9 | 13.6 | 17.0 | 38.1 |
| 18 × 210 | 16.3 | 1.5 | 11.0 | 13.6 | 17.0 | 50.8 |
| 19 × 210 | 17.6 | 1.5 | 12.1 | 14.6 | 18.0 | 50.8 |
| 20 × 210 | 18.9 | 1.5 | 13.2 | 15.6 | 19.0 | 50.8 |
| 22 × 210 | 21.4 | 1.5 | 15.3 | 17.6 | 21.0 | 50.8 |
| 24 × 210 | 24.0 | 1.5 | 17.5 | 19.6 | 23.0 | 50.8 |
| 26 × 210 | 26.6 | 1.5 | 19.4 | 21.6 | 25.0 | 50.8 |
| 28 × 210 | 29.2 | 1.5 | 21.7 | 23.6 | 27.0 | 50.8 |

Figure 17:
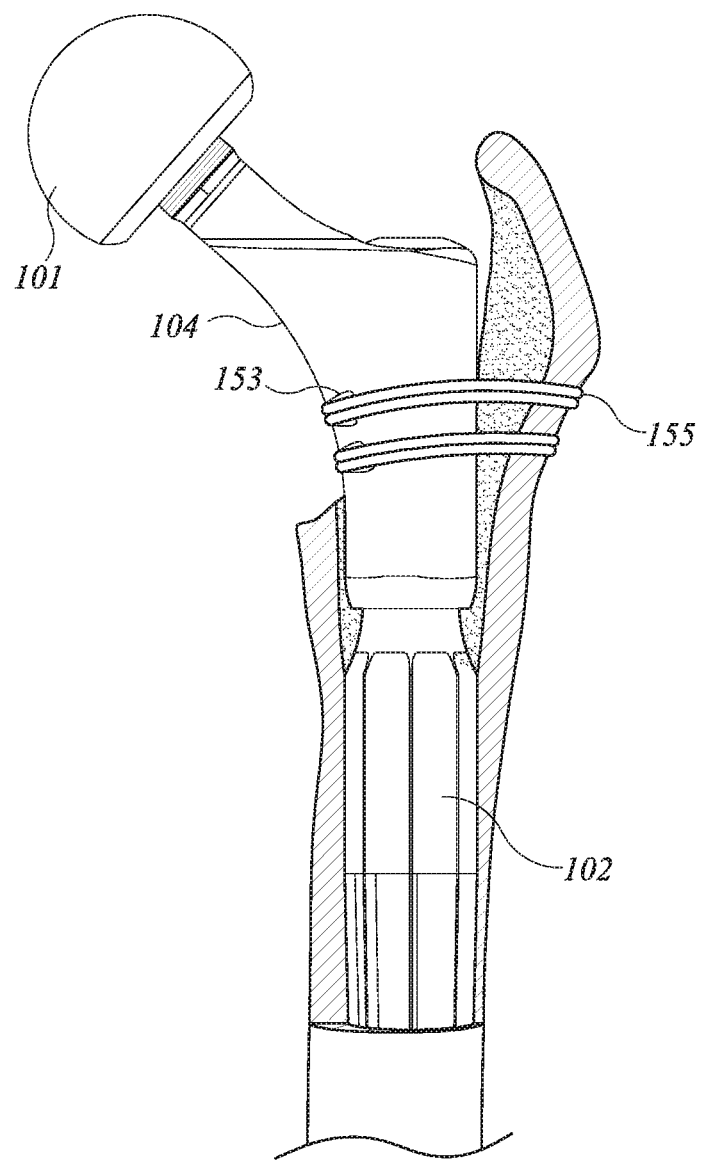
FIG. 17 depicts a front view of a hip implant system positioned within a femur.

FIG. 17 depicts an embodiment of the hip implant system 100 in combination poly cables 155 positioned within a femoral canal. Two poly cables 155 are wrapped around each cable groove 153 of the proximal body 104 and around a section of the femur opposite the cable grooves 153. The cable grooves 153 can be configured to prevent slippage of the poly cables 155 along the proximal body 104. The poly cables 155 can be wrapped around the proximal body 104 and the femur to restrict or prevent relative movement of the proximal body 104 with respect to the femur.

Figure 18:
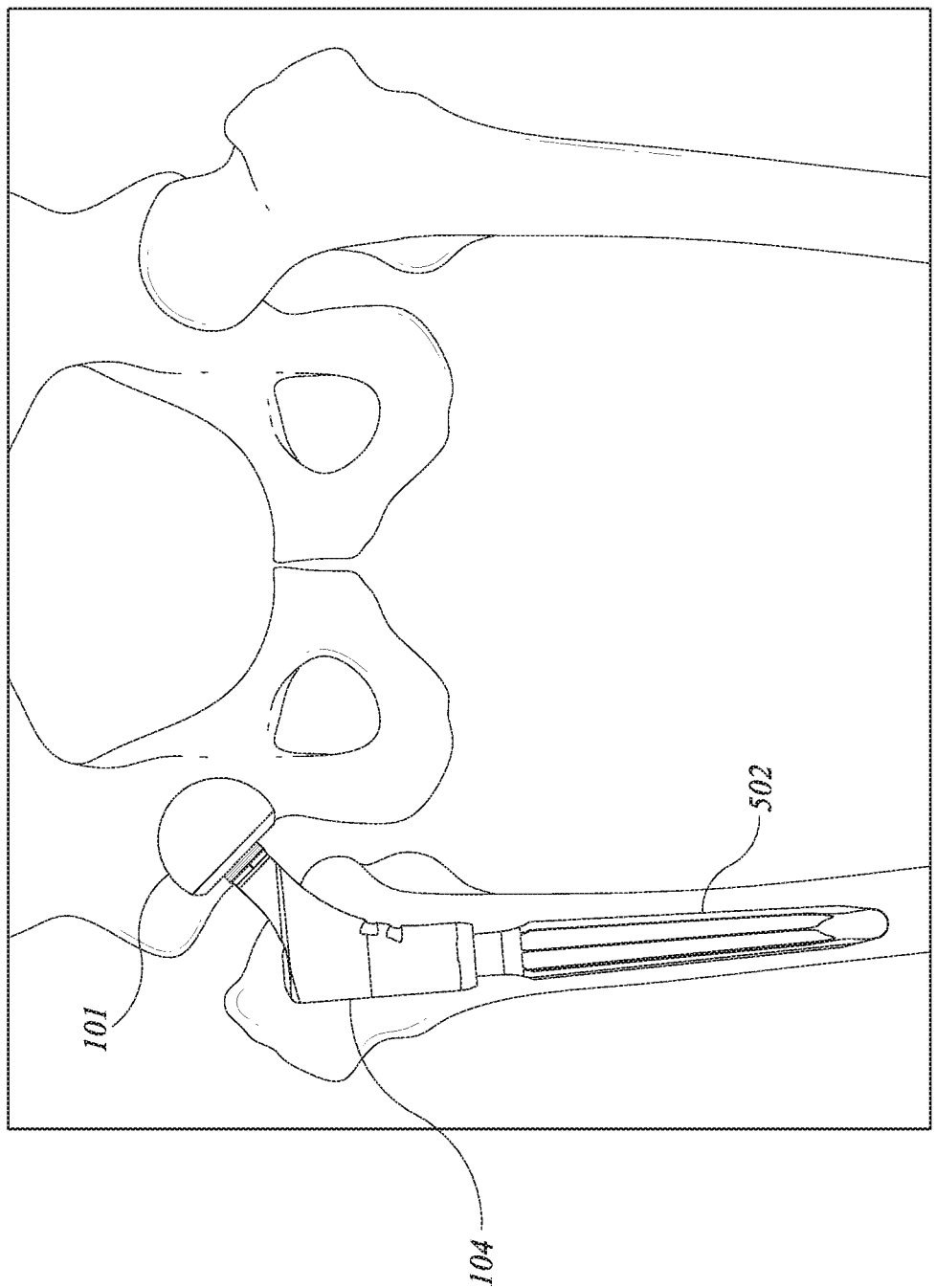
FIG. 18 depicts a front view of a hip implant system positioned within a body.

FIG. 18 depicts an embodiment of the hip implant system 500 in combination with a femoral head 101 positioned within a body of patient. As shown in FIG. 18, the distal stem 102 is positioned with a femoral canal of a femur of a right leg of the patient. The proximal body 104 is oriented so that the neck of the proximal body 104 extends medially towards an acetabulum on the right side of the pelvis of the patient. Upon fully seating the implant stem to the desired reamed depth, the outer diameter of the longitudinal fins are larger than the corresponding reamed hole. In other words, when the implant stem is positioned in the reamed femoral canal, the fins interfere with (that is, extend into or "bite" into) the cortical wall of the reamed bone by an amount equal to or less than the height of the fins. In some embodiments, at least a portion of the fins extend into the cortical wall by (radially) 0.10 mm or less, 0.20 mm or less, or up to the amount of the fin height. For example, the at least a portion of the fins may extend into the cortical wall by 0.20 mm radially (diametrically 0.40 mm, that is, 0.20 mm per side).

The hip implant systems described herein can be made of any material suitable for implant into the human body. For example, titanium, titanium alloy, cobalt chrome (CoCr), stainless steel, or a ceramic material, or a combination of such materials. The components of the hip implant systems described herein can be variously sized or shaped, in addition to what is explicitly describe herein, to increase their functionality and/or suitability for hip replacement. For example, the length of the distal stem can be 130 mm, 170 mm, 210 mm, less than 130 mm, between 130 mm to 170 mm, between 170 mm to 210 mm, greater than 210 mm, or any other suitable length.

The hip implant systems described herein can be utilized to treat a variety of hip issues including, but not limited to, non-inflammatory degenerative joint disease, including osteoarthritis and avascular necrosis of the natural femoral head, rheumatoid arthritis, functional deformities, femoral fracture, trochanteric fracture, and previously failed surgical attempts.

An exemplary method of implanting the hip implant systems described herein can include one or more of the following steps. First, the femur of a patient can be reamed until cortical chatter is detected at a depth corresponding to a desired stem length. In some embodiments, the femur can be reamed sequentially using reamers of increasing size. After cortical chatter is detected, the femoral canal can be evaluated for positioning of an anterior relief of a distal stem of the hip implant system. After the femoral canal is evaluated, the distal stem of the hip implant system can be inserted into the femoral canal. The anterior relief can be positioned to accommodate the shape of an interior wall of the femoral canal. It may desirable to position the anterior relief to avoid the anterior cortex of the femur or to accommodate one or more deformities. Following insertion of the distal stem, a proximal body reamer can be used to remove bone at the medial base of the greater trochanter to facilitate trialing and implanting of a proximal body of the hip implant system. After use of the proximal body reamer, a trial proximal body can be secured to the implanted stem. Following securement of the trial proximal body to the stem, the range of motion and stability using the trial proximal body can be assessed. If the trial proximal body provides a desired range of motion and stability, the trial proximal body can be implanted and secured with a fastener. If the trial proximal body does not provide the desired range of motion and stability, the trial proximal body can be removed and replaced with additional proximal bodies until a desired match is found.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

Headings are included herein for reference and to aid in locating various sections. These headings are not intended to limit the scope of the concepts described with respect thereto. Such concepts may have applicability throughout the entire specification.

The previous description of the disclosed implementations is provided to enable any person skilled in the art to make or use the present disclosure. Various modifications to these implementations will be readily apparent to those skilled in the art, and the generic principles defined herein may be applied to other implementations without departing from the spirit or scope of the disclosure. Thus, the present disclosure is not intended to be limited to the implementations shown herein but is to be accorded the widest scope consistent with the principles and novel features disclosed herein.

What is claimed is:

1. A hip implant system comprising:
    an elongated distal stem having
        a tapered trunnion comprising
            a proximal end, a distal end, and a longitudinal axis extending therebetween; and
            an inner cavity defined by an interior surface of the tapered trunnion and extending from the proximal end of the tapered trunnion at least partially toward the distal end of the tapered trunnion through at least a portion of the tapered trunnion, wherein the interior surface of the tapered trunnion comprises a threaded portion configured to mate with a threaded end of a fastener; and
        a stem body comprising a proximal end and a distal end, the stem body extending distally from the tapered trunnion; and
    a proximal body having
        a body distal end;
        a first opening on one side of the proximal body at the body distal end;
        a second opening on the exterior of the proximal body, positioned opposite the first opening on the other side of the proximal body;
        an inner cavity extending in the proximal body between the first opening and the second opening, the inner cavity defined by an interior surface of the proximal body, wherein the inner cavity comprises
            a first inner cavity section positioned proximal to the first opening, wherein the proximal body is configured to receive the proximal end of the tapered trunnion of the distal stem through the first opening and within the first inner cavity section;
            a second inner cavity section positioned between the first inner cavity section and the second opening, wherein the interior surface in the second inner cavity section comprises a circumference smaller than a circumference of the interior surface in the first inner cavity section and larger than a circumference of the fastener, wherein the circumference of the interior surface in the second inner cavity section is smaller than an outer circumference of the proximal end of the tapered trunnion of the distal stem, and wherein the second inner cavity section is configured to receive a threaded body of the fastener, wherein the interior surface of the proximal body at the second inner cavity section comprises a threaded section configured to mate with a threaded bolt of a taper breaker; and
            a third inner cavity section positioned proximal to the threaded section of the second inner cavity section and between the second opening of the proximal body and the second inner cavity section;
        a spherical rim extending from an outer edge of the second opening on an exterior surface of the proximal body to the third inner cavity section;
        a neck portion extending laterally and proximally from a side of the proximal body, the neck portion being configured to engage a femoral head; and
    the fastener having
        a head configured to engage a tool for tightening and loosening the fastener, the head comprising an exterior surface having a spherical portion conforming to the shape of the proximal body spherical rim, the spherical portion of the head contacting the spherical rim of the proximal body to align and seat the head of the fastener in the proximal body at the second opening of the proximal body when the fastener is connected to the threaded portion of the tapered trunnion;
        a threaded end; and
        a shaft extending between the head and the threaded end, wherein at least a portion of the threaded end is configured to extend through the third inner cavity section and the second inner cavity section, the threaded end not engaging the threaded section of the second inner cavity section, and mate with the threaded portion of the interior surface of the tapered trunnion.

2. The hip implant system of claim 1, wherein the distal stem comprises a plurality of fins disposed on the exterior surface of the stem body running along at least a portion of the distal stem.

3. The hip implant system of claim 2, wherein the plurality of fins includes at least three fins.

4. The hip implant system of claim 2, wherein the plurality of fins includes at least 8 fins.

5. The hip implant system of claim 2, wherein at least a portion of each of the plurality of fins are 1.5 mm or less in height.

6. The hip implant system of claim 2, wherein at least a portion of each of the plurality of fins are less than 2.5 mm in height.

7. The hip system of claim 2, wherein the plurality of fins, and a reamed femoral canal into which the distal stem is positioned, are sized such that at least a portion of the plurality of fins extend into the canal wall at least 0.2 mm.

8. The hip system of claim 1, wherein the stem body comprises a tapered first body section having a proximal end, a distal end, and a longitudinal axis extending therebetween.

9. The hip system of claim 8, wherein the distal end of the tapered first body section comprises a partially rounded distal tip comprising:
    a front section; and
    a rear section, the front and rear sections separated by a coronal plane extending through the tapered first body section from a proximal end of the tapered first body section to the distal end of the tapered first body section, wherein the rear section of the distal tip is characterized by a partially spherical shape, wherein the front section of the distal tip comprises an anterior relief having an elongated face having a rounded distal edge, wherein at least a portion of the anterior relief is configured to taper towards the distal end at a greater angle than a segment of the first body section immediately proximal to the anterior relief.

10. The hip system of claim 8, wherein the stem body comprises a second body section having a proximal end, a distal end, and a longitudinal axis extending therebetween, the second body section extending between the distal end of the tapered trunnion and the proximal end of the first body section.

11. The hip system of claim 10, wherein the longitudinal axis of the tapered first body section is positioned at a non-zero angle to the longitudinal axis of the second body section.

12. The hip system of claim 10, wherein the second body section is generally cylindrical.

13. The hip system of claim 1, wherein an exterior surface of the proximal body comprises at least one groove a portion of the proximal body aligned with the first inner cavity.

14. The hip system of claim 13, wherein the at least one groove is configured to receive at least one cable in the groove to prevent the cable from moving in at least one direction on the exterior surface of the proximal body.

15. The hip system of claim 13, wherein the at least one groove is configured to receive at least one poly cable such that a portion of the at least one poly cable extends into at least a portion of the groove.

16. The hip system of claim 13, wherein the at least one groove is configured to receive two or more poly cables such that a portion of the two or more poly cable extends into at least a portion of the at least one groove.

17. The hip system of claim 13, wherein the at least one groove is at least 0.5 mm deep.

18. The hip system of claim 13, wherein the at least one groove is at least 0.5 mm wide.

19. The hip system of claim 13, wherein the at least one groove is arranged along a surface of a connection portion of the proximal body and along an edge of the proximal body between the neck and the distal end of the proximal body.

20. The hip system of claim 1, wherein the fastener comprises a spherical locking bolt.

21. The hip implant system of claim 1, wherein the third inner cavity has a circumference greater than the circumference of the second inner cavity to allow for the passage of a portion of the fastener or to receive a tool.

22. The hip implant system of claim 1, wherein the third inner cavity has a cross-sectional area greater than the cross-sectional area of the second inner cavity to allow for the passage of the fastener or to receive a tool.

* * * * *

UNITED STATES PATENT AND TRADEMARK OFFICE
CERTIFICATE OF CORRECTION

PATENT NO. : 11,039,930 B2  
APPLICATION NO. : 15/901823  
DATED : June 22, 2021  
INVENTOR(S) : Adam Shallenberg Page 1 of 1

It is certified that error appears in the above-identified patent and that said Letters Patent is hereby corrected as shown below:

On the Title Page

Item [71], delete "L.P." and insert --L.P. (D/B/A DJO Surgical)--.

Item [73], delete "L.P." and insert --L.P. (D/B/A DJO Surgical)--.

In the Specification

Column 6, Line 38, delete "X-Alt™" and insert --X-alt™--.

Column 14, Line 20, delete "5c." and insert --5C.--.

Column 14, Line 56, delete "the a" and insert --the--.

Column 15, Line 5, delete "FIG." and insert --FIGS.--.

Column 17, Line 32, delete "FIG." and insert --FIGS.--.

Column 18, Line 36, delete "of the of the" and insert --of the--.

Column 21, Line 46, delete "11.9" and insert --11.0--.

Column 22, Line 48, delete "may" and insert --may be--.

Signed and Sealed this  
Thirty-first Day of August, 2021

Drew Hirshfeld  
*Performing the Functions and Duties of the*  
*Under Secretary of Commerce for Intellectual Property and*  
*Director of the United States Patent and Trademark Office*